(12) United States Patent
Carpenter et al.

(10) Patent No.: US 7,846,177 B2
(45) Date of Patent: Dec. 7, 2010

(54) SURGICAL DEVICE

(75) Inventors: David Carpenter, Jaffrey, NH (US);
Erin-Anne Lemieux, Milford, NH (US);
Brooke Skora, Chicago, IL (US); David J. Booth, Lawrenceville, GA (US);
Robert F. Leonard, Atlanta, GA (US);
Anthony Looper, Lake Zurich, IL (US);
Joseph Tommasini, Conyers, GA (US)

(73) Assignee: CareFusion 2200, Inc., San Diego, CA (US)

( * ) Notice: Subject to any disclaimer, the term of this patent is extended or adjusted under 35 U.S.C. 154(b) by 1199 days.

(21) Appl. No.: 11/474,792

(22) Filed: Jun. 26, 2006

(65) Prior Publication Data

US 2007/0299469 A1    Dec. 27, 2007

(51) Int. Cl.
*A61B 17/00* (2006.01)
(52) U.S. Cl. ...................................... 606/205
(58) Field of Classification Search ........... 606/205, 606/206, 207, 208
See application file for complete search history.

(56) References Cited

U.S. PATENT DOCUMENTS

| 3,608,544 | A |   | 9/1971 | Schnepper | 128/2 R |
|---|---|---|---|---|---|
| 4,440,170 | A |   | 4/1984 | Golden et al. | 128/325 |
| 4,483,562 | A |   | 11/1984 | Schoolman | 294/19 |
| 4,590,936 | A |   | 5/1986 | Straub et al. | 128/305 |
| 4,813,407 | A |   | 3/1989 | Vogen | |
| 5,112,299 | A |   | 5/1992 | Pascaloff | |
| 5,147,357 | A | * | 9/1992 | Rose et al. | 606/49 |
| 5,174,300 | A |   | 12/1992 | Bales et al. | 128/751 |
| 5,176,702 | A | * | 1/1993 | Bales et al. | 606/208 |
| 5,234,460 | A |   | 8/1993 | Stouder, Jr. | 606/205 |
| 5,251,638 | A |   | 10/1993 | Cottoner, Jr. et al. | 128/751 |
| D349,341 | S |   | 8/1994 | Lichtman et al. | D24/143 |
| 5,342,391 | A | * | 8/1994 | Foshee et al. | 606/205 |
| 5,370,659 | A |   | 12/1994 | Sakashita | 606/205 |
| 5,409,478 | A |   | 4/1995 | Gerry et al. | 606/1 |
| 5,470,328 | A |   | 11/1995 | Furnish et al. | 606/1 |
| 5,476,479 | A |   | 12/1995 | Green et al. | 606/205 |
| 5,478,351 | A |   | 12/1995 | Meade et al. | 606/205 |
| 5,480,409 | A |   | 1/1996 | Riza | 606/205 |
| 5,483,952 | A |   | 1/1996 | Aranyi | 600/131 |
| 5,498,256 | A |   | 3/1996 | Furnish | 606/1 |
| 5,562,655 | A |   | 10/1996 | Mittelstadt et al. | 606/1 |

(Continued)

FOREIGN PATENT DOCUMENTS

DE    103 53 552 A1    10/1998

(Continued)

OTHER PUBLICATIONS

Information Sheet—"The MicroLine Handpiece", for handpieces and related tips, undated, 1 page.

(Continued)

*Primary Examiner*—Todd E Manahan
*Assistant Examiner*—Naquan Ishman
(74) *Attorney, Agent, or Firm*—Brinks Hofer Gilson & Lione

(57) ABSTRACT

A laparoscopic surgical device is provided, including a ratchet mechanism. The ratchet mechanism includes a single button or lever that may be used to release or defeat a ratchet engagement.

24 Claims, 24 Drawing Sheets

U.S. PATENT DOCUMENTS

| | | | | |
|---|---|---|---|---|
| 5,562,682 | A | 10/1996 | Oberlin et al. | 606/139 |
| 5,569,269 | A * | 10/1996 | Hart et al. | 606/144 |
| 5,582,615 | A | 12/1996 | Foshee et al. | 606/139 |
| 5,603,723 | A * | 2/1997 | Aranyi et al. | 606/205 |
| 5,609,601 | A | 3/1997 | Kolesa et al. | 606/170 |
| 5,626,608 | A | 5/1997 | Cuny et al. | 606/205 |
| 5,665,105 | A | 9/1997 | Furnish et al. | 606/205 |
| 5,725,536 | A | 3/1998 | Oberlin et al. | 606/139 |
| 5,728,121 | A * | 3/1998 | Bimbo et al. | 606/207 |
| 5,735,874 | A | 4/1998 | Measamer et al. | |
| 5,743,456 | A | 4/1998 | Jones et al. | |
| 5,782,749 | A | 7/1998 | Riza | |
| 5,797,956 | A | 8/1998 | Furnish et al. | |
| 5,827,263 | A | 10/1998 | Furnish et al. | |
| 5,827,323 | A | 10/1998 | Klieman et al. | |
| 5,830,231 | A | 11/1998 | Geiges, Jr. | |
| 5,836,960 | A | 11/1998 | Kolesa et al. | |
| 5,843,122 | A | 12/1998 | Riza | |
| 5,868,784 | A | 2/1999 | Riza | |
| 5,868,785 | A | 2/1999 | Tal et al. | |
| 5,871,488 | A | 2/1999 | Tovey et al. | |
| 5,911,736 | A | 6/1999 | Dingler et al. | |
| 5,922,007 | A | 7/1999 | Hoogeboom et al. | |
| 5,925,064 | A | 7/1999 | Meyers et al. | |
| 5,928,256 | A | 7/1999 | Riza | |
| 5,928,263 | A | 7/1999 | Hoogeboom | |
| 5,935,126 | A | 8/1999 | Riza | |
| 5,938,667 | A | 8/1999 | Peyser et al. | |
| 5,938,685 | A | 8/1999 | Giurtino | |
| 5,980,511 | A | 11/1999 | Bilitz et al. | |
| 6,000,138 | A * | 12/1999 | Bornancini | 30/232 |
| 6,039,752 | A | 3/2000 | Kimiura et al. | |
| 6,102,925 | A | 8/2000 | Oren et al. | |
| 6,117,158 | A | 9/2000 | Measamer et al. | |
| 6,139,563 | A | 10/2000 | Cosgrove, III et al. | |
| 6,146,391 | A | 11/2000 | Cigaina | |
| 6,146,392 | A | 11/2000 | Smith | |
| 6,168,605 | B1 | 1/2001 | Measamer et al. | |
| 6,171,316 | B1 | 1/2001 | Kovac et al. | |
| 6,187,026 | B1 | 2/2001 | Devlin et al. | |
| 6,280,458 | B1 | 8/2001 | Boche et al. | |
| 6,299,625 | B1 | 10/2001 | Bacher | |
| 6,358,267 | B1 * | 3/2002 | Murakami et al. | 606/205 |
| 6,358,268 | B1 | 3/2002 | Hunt et al. | |
| 6,440,144 | B1 | 8/2002 | Bacher | |
| 6,506,208 | B2 | 1/2003 | Hunt et al. | |
| 6,524,238 | B2 | 2/2003 | Velikaris et al. | |
| 6,584,693 | B2 | 7/2003 | DeBolt | |
| 6,605,036 | B1 | 8/2003 | Wild | |
| 6,620,184 | B2 | 9/2003 | deLaforcade et al. | |
| 6,626,929 | B1 | 9/2003 | Bannerman | |
| 6,635,071 | B2 | 10/2003 | Boche et al. | |
| 6,641,595 | B1 | 11/2003 | Moran et al. | |
| 6,663,641 | B1 | 12/2003 | Kovac et al. | |
| 6,676,120 | B1 | 1/2004 | Hallbeck et al. | |
| 2004/0167569 | A1 | 8/2004 | Dicesare et al. | 606/208 |
| 2004/0225323 | A1 | 11/2004 | Nagase et al. | 606/205 |
| 2004/0254605 | A1 | 12/2004 | DiFrancesco et al. | 606/205 |
| 2004/0260314 | A1 | 12/2004 | Lizardi et al. | 606/14 |

FOREIGN PATENT DOCUMENTS

| | | | |
|---|---|---|---|
| EP | 0 555 105 | A | 8/1993 |
| EP | 0 702 937 | A | 3/1996 |
| EP | 0 813 843 | A | 12/1997 |
| EP | 1 498 075 | A | 1/2005 |
| WO | WO 01/89396 | | 11/2001 |

OTHER PUBLICATIONS

Informational Literature—"Logic Laparoscopic Instrument System", by Surgical Innovations Limited, Leeds, England, undated, 4 pages.

Catalog Pages—AdTec Monopolar endoscopic surgical instruments, Aesculap, undated, 3 pages.

Information Sheet—"DetachaTip® System Multi-Use Endoscopic System", Conmed Corporation, undated.

Informational Literature—Aesculap, Various surgical instruments for use during general gynecological and laparoscopic procedures, undated, 5 pages.

Instructions for various endoscopic surgical instruments, Olympus," HiQ+ The Intelligent Line", undated, 5 pages.

Instruction booklet for Assembly, use and sterilization of "DetachaTip® System Multi-Use Endoscopic System", Conmed Corporation, undated, various languages, 8 pages.

Instruction Sheet for MicroLine "Re-New IV Laparoscopic hand Pieces" and Electrocautery surgical instruments, P/N 09-39-36 Rev. Original issue, Oct. 2002, ECO#583, 2 pages.

Informational Literature, "Storz Karl Storz—Endoskope", Various handles for endoscopic surgical instruments, undated, 4 pages.

* cited by examiner

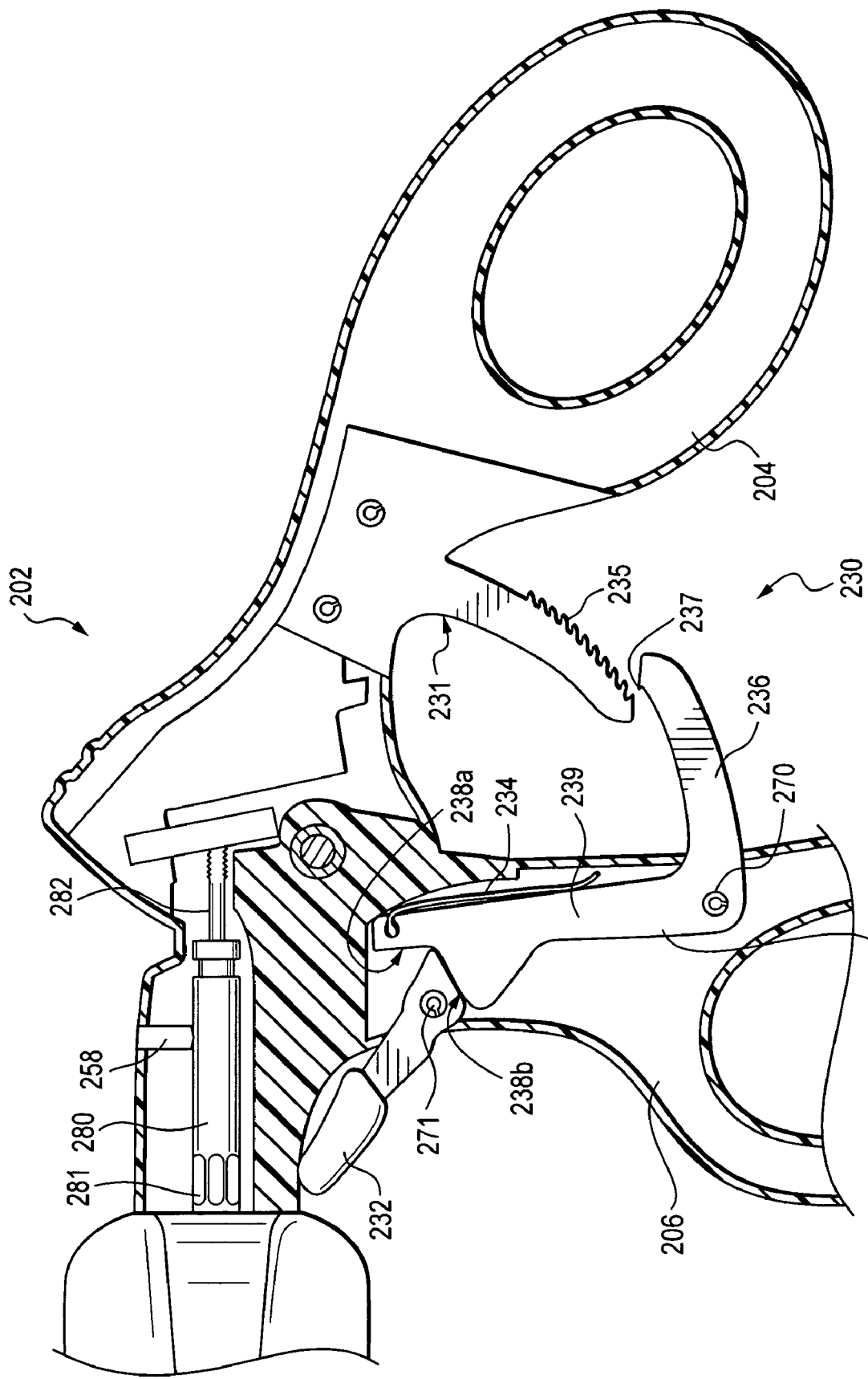

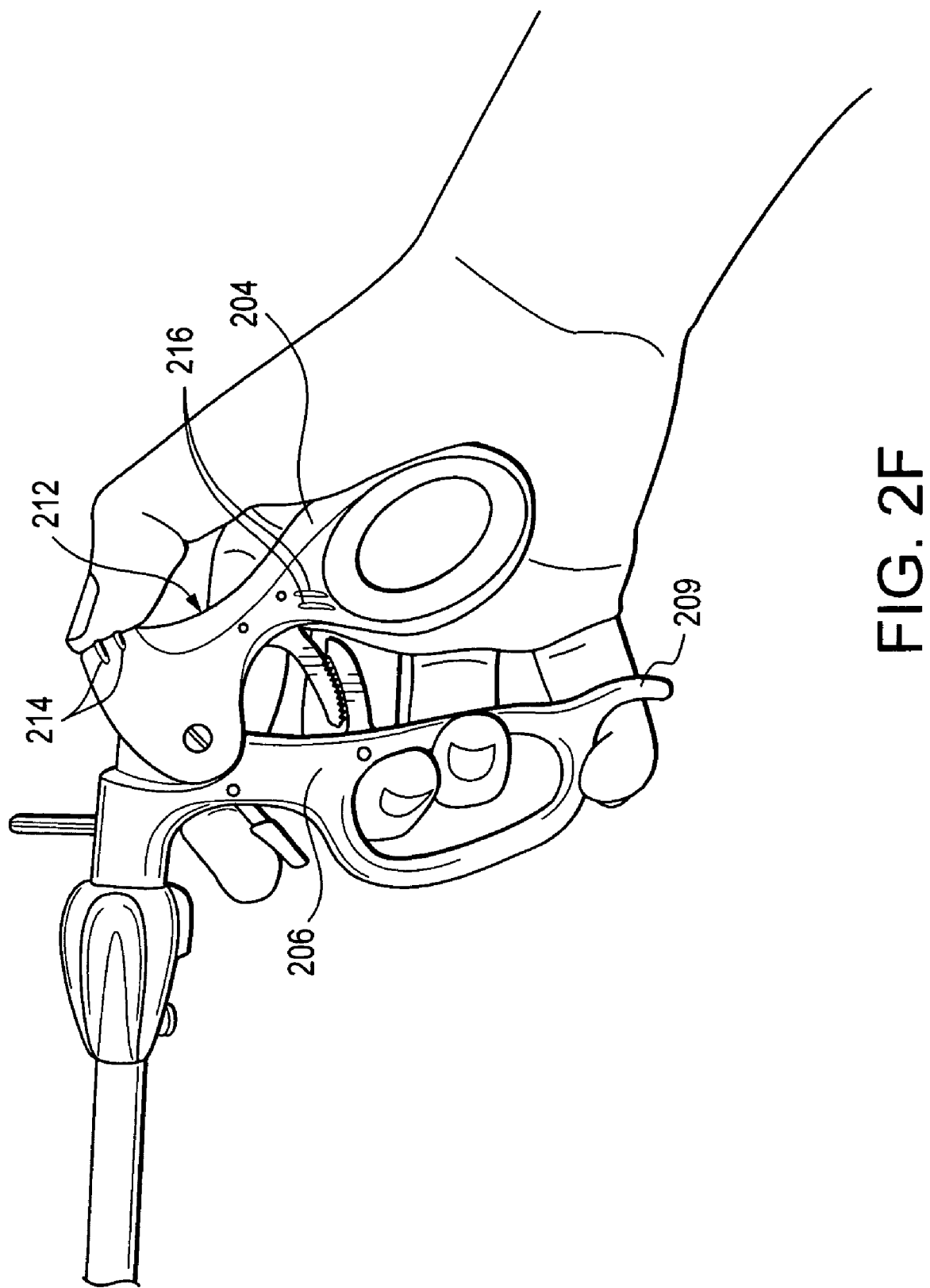

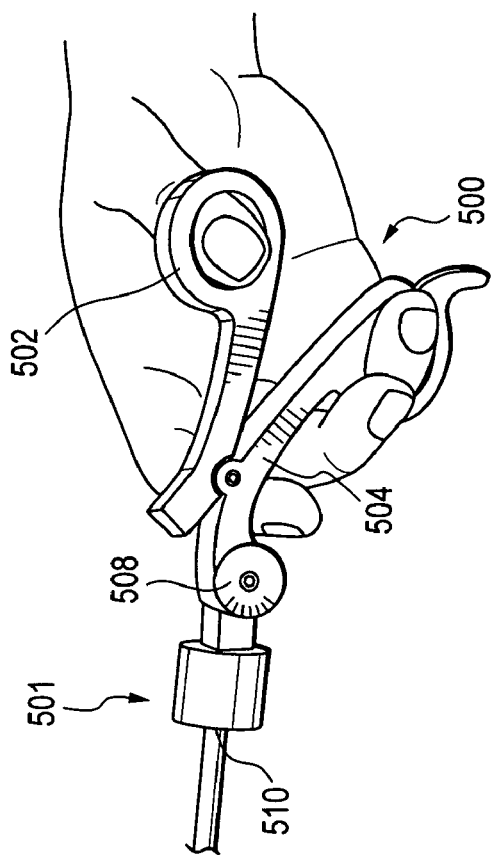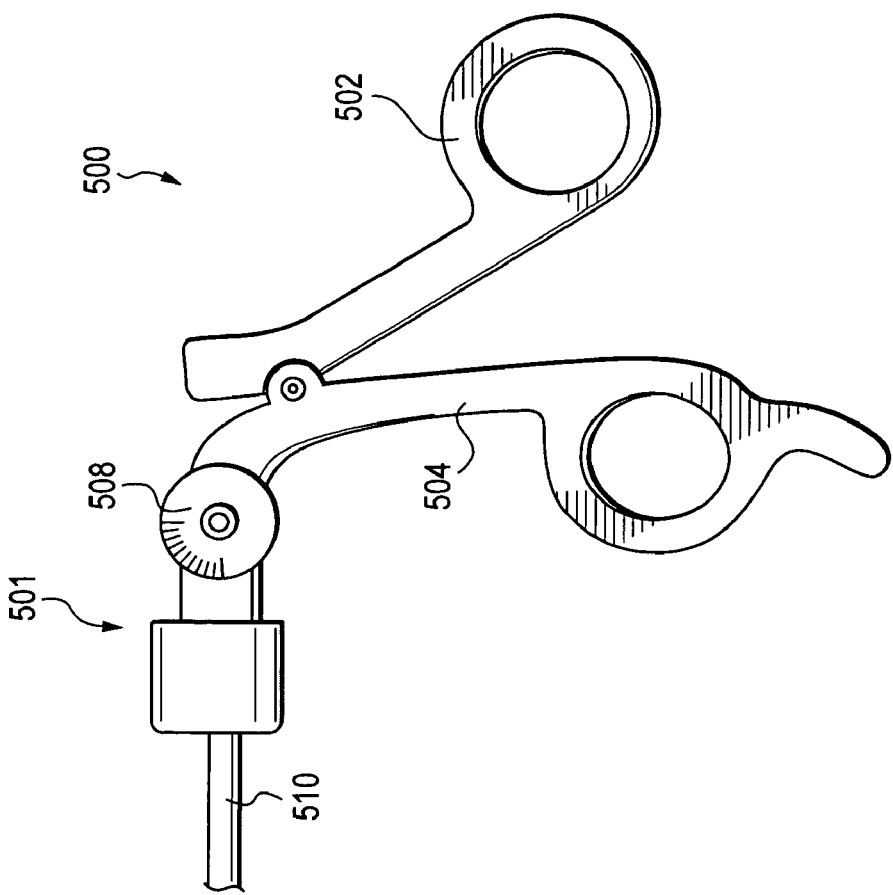
FIG. 5A
FIG. 5

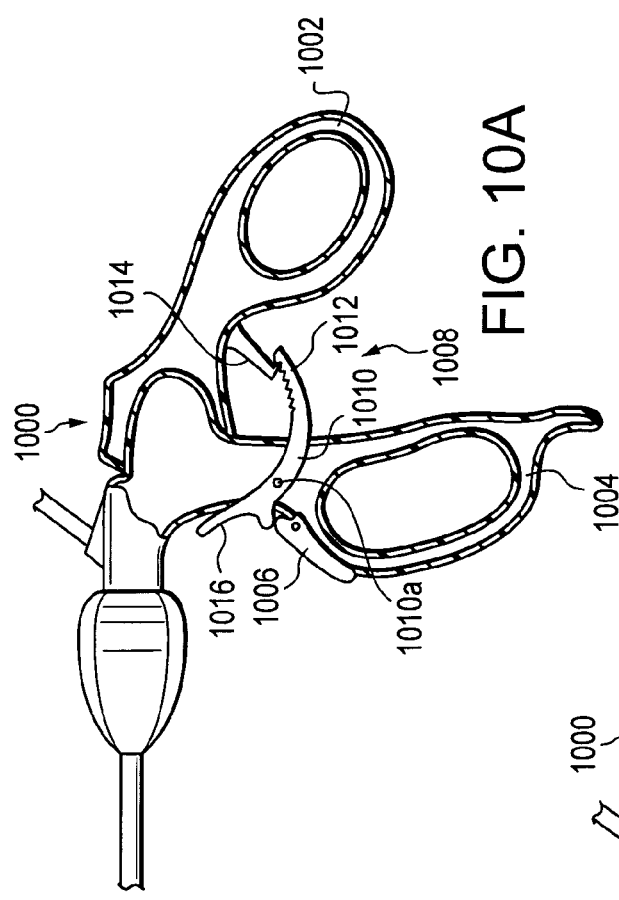
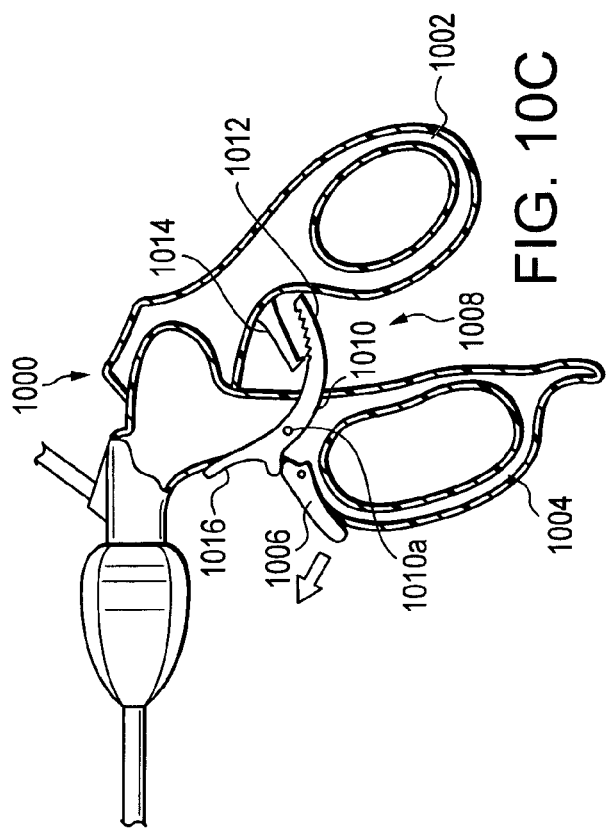
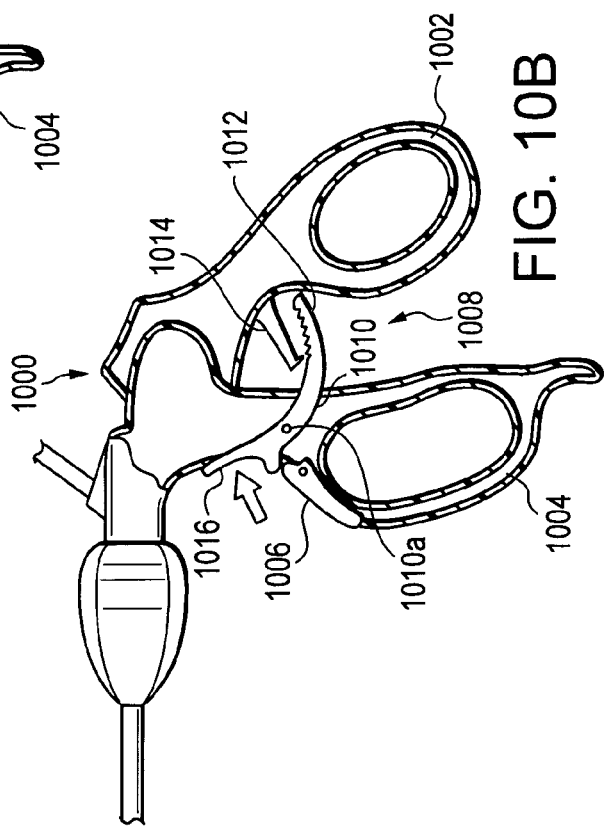

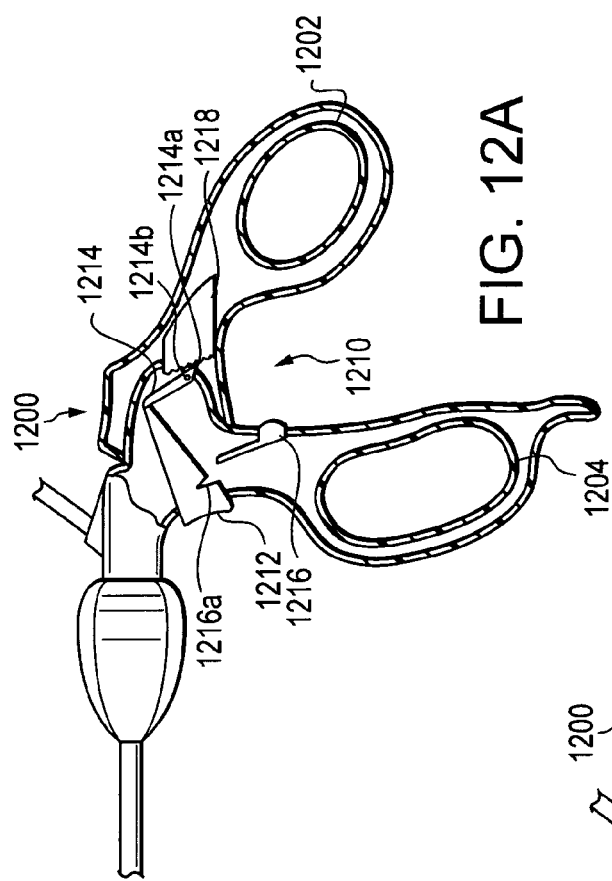
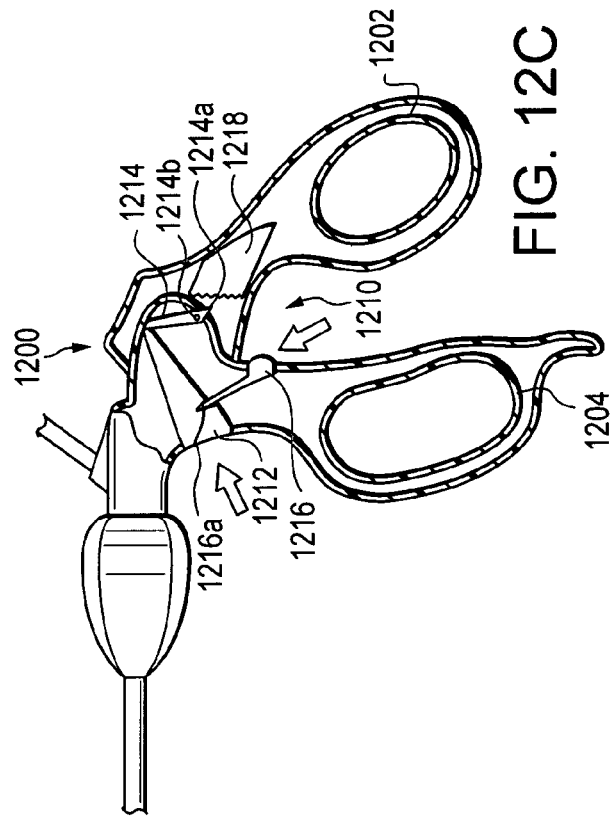
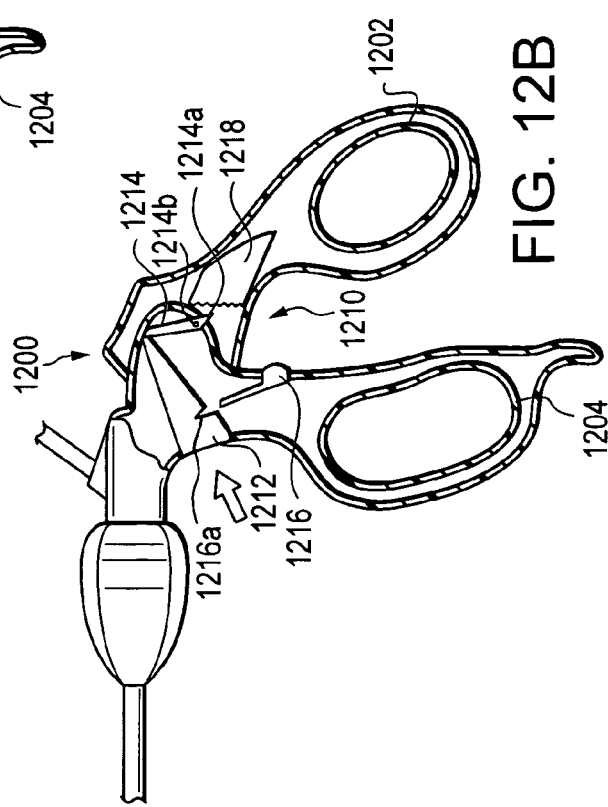

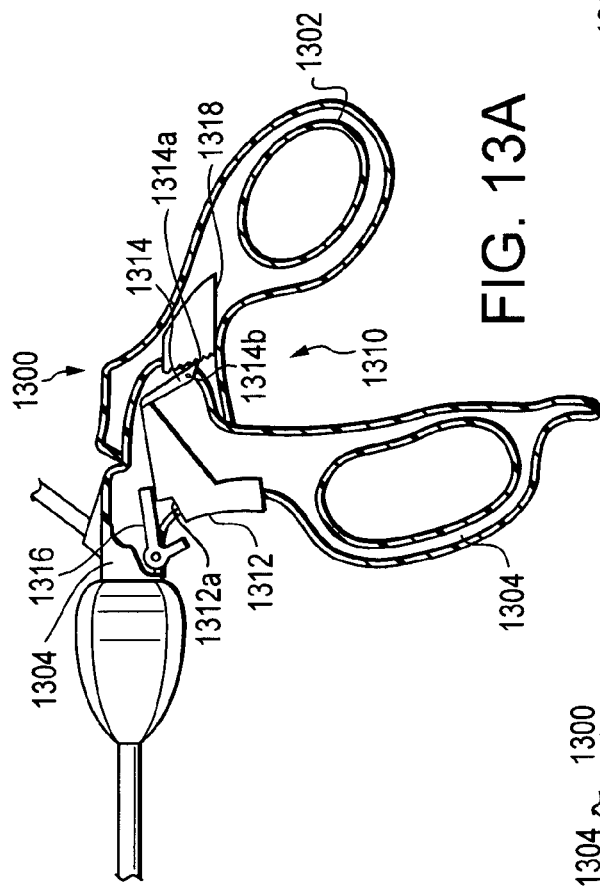
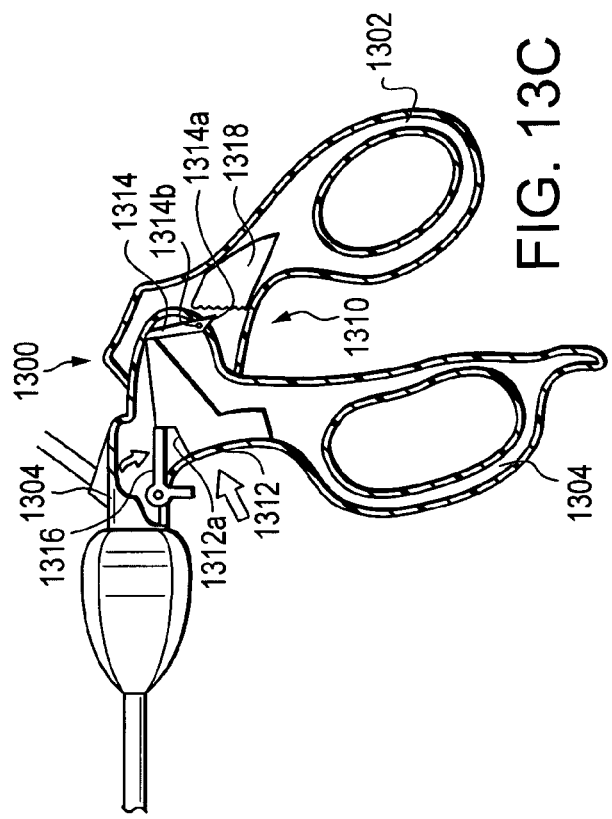
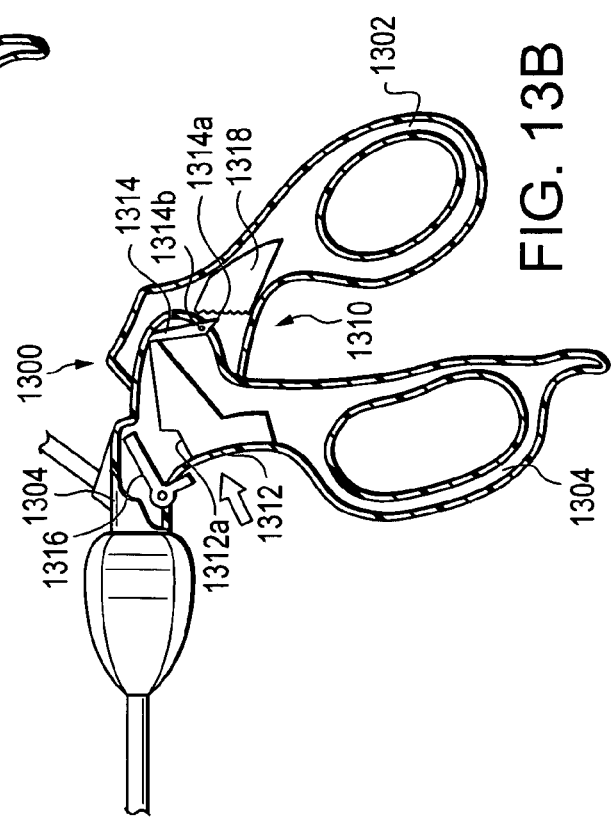
FIG. 13A
FIG. 13B
FIG. 13C

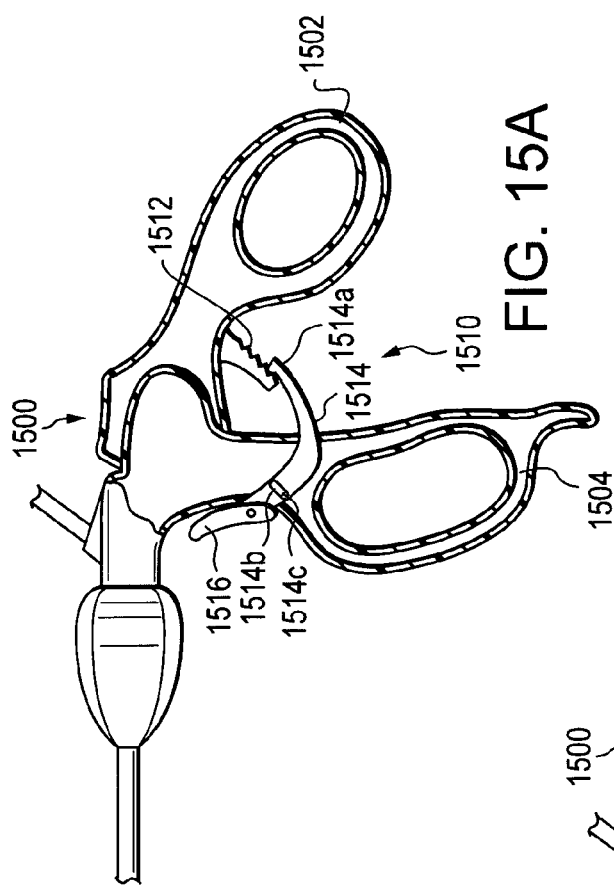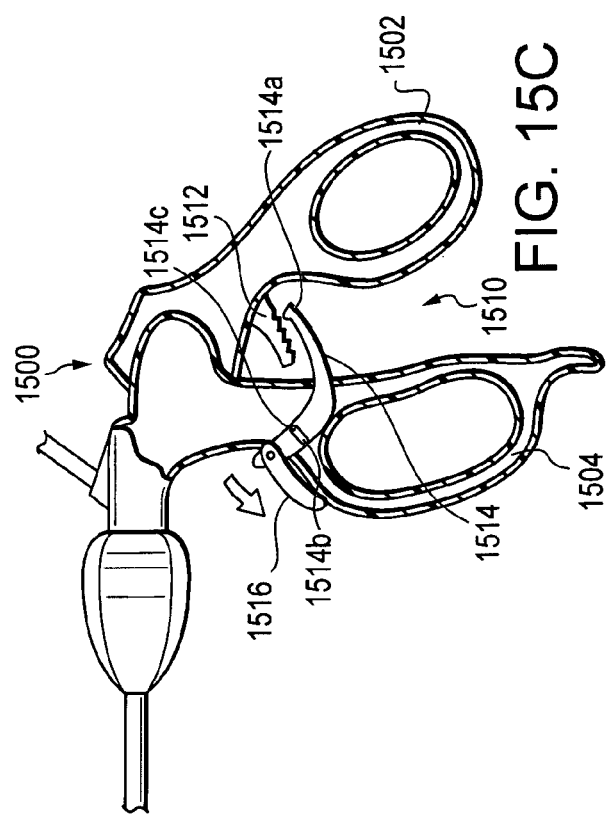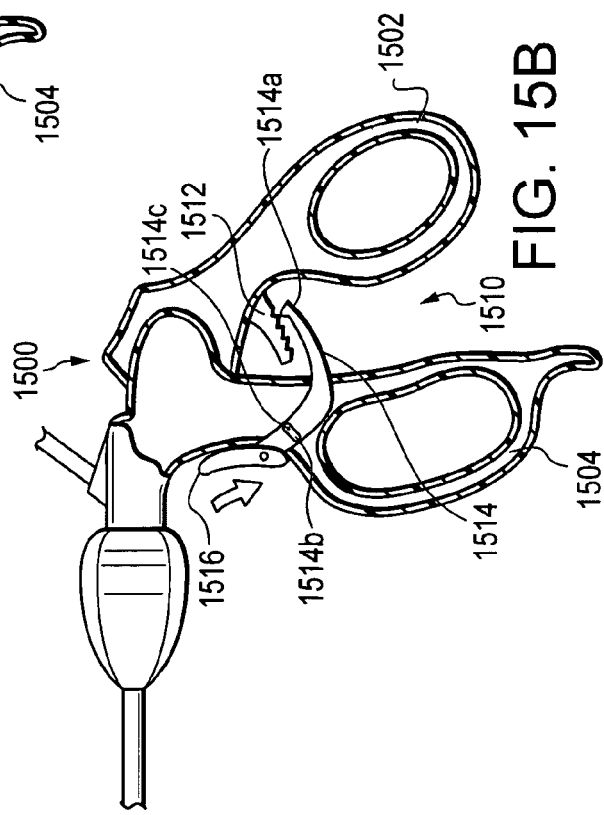

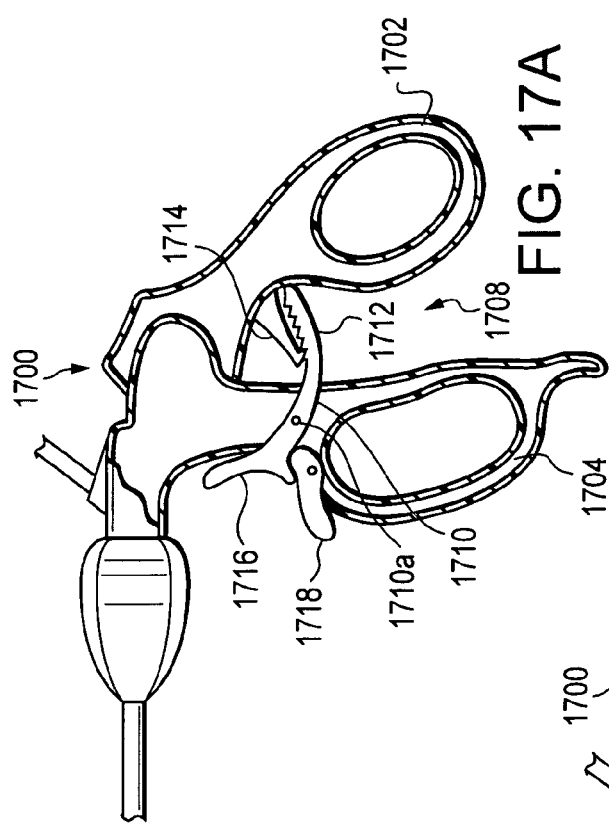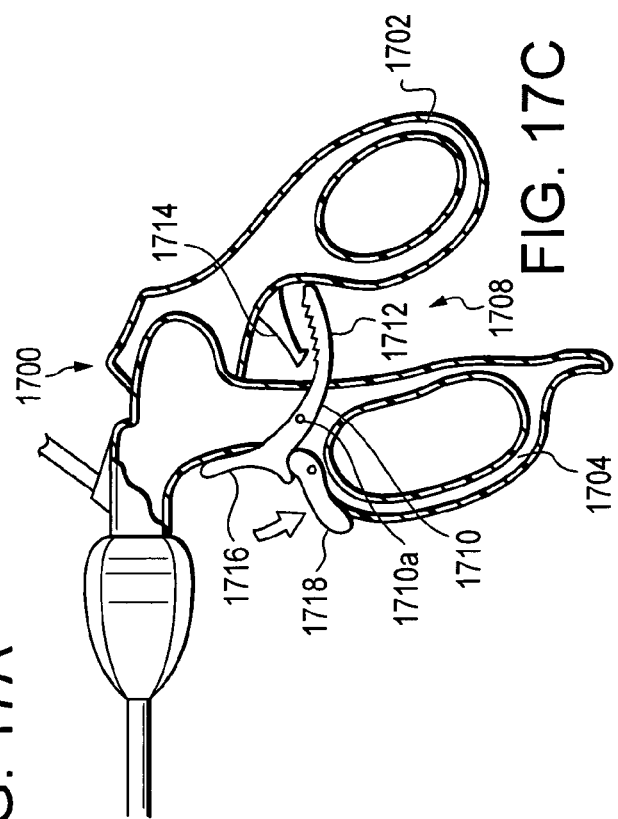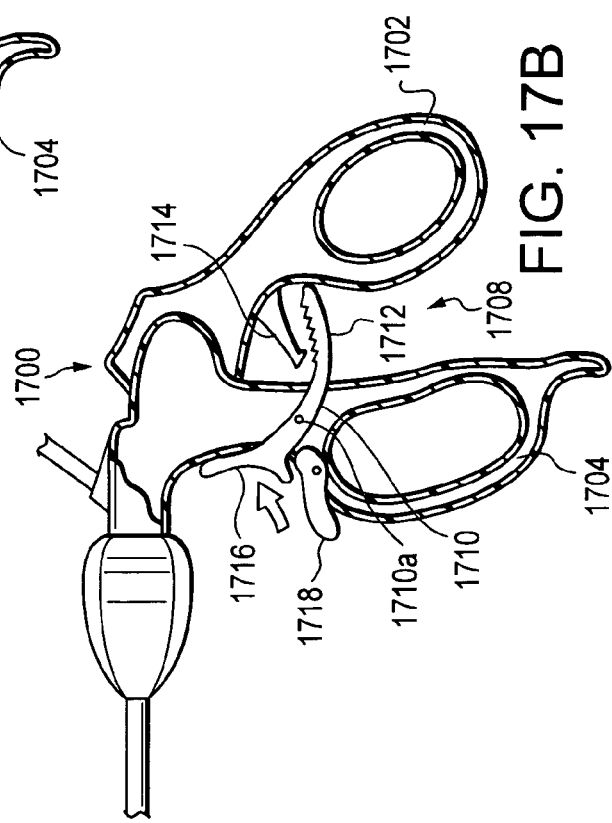

SURGICAL DEVICE

FIELD OF THE INVENTION

The present invention relates generally to medical devices, and more particularly to a handle configured to manipulate a distal tool end of a laparoscopic device.

BACKGROUND

As depicted in FIG. 1, a typical monopolar electrosurgical laparoscopic tool device 100 generally has five main components: a handle 102, an outer shaft 104 extending longitudinally from the handle, an actuation rod 106 extending through the outer shaft, an electrode 108 in electroconductive contact with the actuation rod, and an actuatable end effector 110, disposed at the distal end of the device. The handle 102 illustrated is a "ring handle", which has a stationary finger portion 112 attached to the outer shaft 104 and an actuatable thumb portion 114 attached to the actuation rod 106. Actuation of the thumb portion 114 by pivoting relative to the finger portion 112 moves the actuation rod 106 axially within the outer shaft 104 to operate the end effector 110. Although many different variations of each of the above components have been introduced into the art, there exists a need for designs that provide efficiency in manufacturing, and that provide surgeons and other users with ergonomic features to enhance safety and ease of use. In particular, there is a need for a handle design that includes an easy-to-use locking feature with a minimal number of components to provide for ease of assembly and durability.

BRIEF SUMMARY

Embodiments of the present invention are configured to address the needs in the art for ergonomic designs that present advantages in manufacture and use. Preferred embodiments of the present invention are configured such that they may be sterilized and reused. The most preferred embodiments of the present invention include a ratchet mechanism that is biased so as to engage the handle members with each other, and that can be released or defeated using a single button or lever. This provides an advantage over many of the prior art ratchet mechanisms that require actuation of two or more separate components to engage, release, and defeat a ratchet. While embodiments of the present invention are directed to aspects of the handle for a laparoscopic surgical device, those of skill in the art will appreciate that handle embodiments of the present invention may be used with different shaft configurations and end effectors (e.g., needle holders, clamps, scissors, dissectors, graspers), and that such uses are within the scope of the present invention.

In one aspect, the present invention includes a surgical instrument having a handle operatively connected to an elongate shaft. The handle includes a thumb ring member pivotably connected to a finger ring member, a first engagement member fixed in and projecting generally distally from the thumb ring member, a second engagement member pivotably mounted to and projecting generally proximally from the finger ring member (with a first end portion of the second engagement member being biased into engagement with the first engagement member), and an elongate cam member pivotably connected to the finger ring member. The handle includes an operative contact of the elongate cam member with a second end portion of the second engagement member such that when the elongate cam member is at a first angle relative to the second engagement member, the operative contact is sufficient to pivot the second engagement member so as to overcome the biased engagement of the second engagement member with the first engagement member. And, when the elongate cam member is at a second angle relative to the second engagement member, the operative contact is sufficient to pivot the second engagement member so as to overcome the biased engagement of the second engagement member with the first engagement member and is sufficient to bias the second engagement member out of engagement with the first engagement member.

In another aspect, the present invention includes a surgical instrument having a handle operatively connected to an elongate shaft wherein the handle includes a first handle member pivotably connected to a second handle member and a ratchet mechanism removably engaging the first and second handle members. The ratchet mechanism includes a ratchet-toothed engagement member fixed to and projecting generally distally from the first handle member, an L-shaped pawl member having a camming leg portion and a pawl leg portion generally perpendicular to the camming leg portion. The L-shaped pawl member is pivotably mounted in the second handle member such that the pawl leg portion projects generally proximally from the second handle member, and an upper region of the camming leg portion includes both a generally vertical camming surface and a distally projecting camming surface. A biasing spring is mounted in the second handle member and forms an operative contact with the L-shaped pawl member such that a proximal end region of the pawl leg portion is biased into engagement with the ratchet-toothed engagement member. The ratchet mechanism also includes a cam lever that is pivotably connected to the second handle member. The cam lever has a first operative contact state with the L-shaped pawl member such that when the cam member is disposed at a first angle relative to the L-shaped pawl member, a first operative contact between the cam lever and the distally projecting camming surface is sufficient to pivot the L-shaped pawl member so as to overcome the biased engagement of the pawl leg portion with the ratchet-toothed engagement member. And, when the cam lever is disposed at a second angle relative to the L-shaped pawl member, a second operative contact between the cam lever and the generally vertical camming surface is sufficient to pivot the L-shaped pawl member so as to overcome the biased engagement of the pawl leg portion with the ratchet-toothed engagement member, and the second operative contact is also sufficient to bias the L-shaped pawl member at an angle wherein the pawl leg portion is not engaged with the ratchet-toothed engagement member.

In yet another aspect, the present invention includes a single-button release/defeat ratchet mechanism for a surgical device handle. The single-button release/defeat ratchet mechanism includes a cam button member, a pawl member in operative contact with the cam button member, a biasing member, and a ratchet member. It is configured such that when the mechanism is in a ratchet-engaged state, the cam button member is in a neutral first position, the operative contact is minimal and the biasing member biases the pawl member into engagement with the ratchet member. When the mechanism is in a ratchet-released state, the cam button member is in a second position such that the operative contact resists the bias of the biasing member and releases the pawl member from engagement with the ratchet member. And, when the mechanism is in a ratchet-defeated state, the cam button member is in a third position such that the operative contact biases the pawl member out of engagement with the ratchet member.

In still another aspect, the present invention includes a surgical instrument having a handle operatively connected to an elongate shaft, wherein the handle includes a first handle member pivotably connected to a second handle member; and a ratchet mechanism removably engaging the first and second handle members. The first handle member includes a plurality of raised thumb-grip ridges disposed on an upper proximal surface of the first handle member, and the ridges are configured to provide a frictional gripping surface. In still yet another aspect, the present invention includes a surgical instrument having a handle operatively connected to an elongate shaft, wherein the handle includes a first handle member pivotably connected to a second handle member; and a ratchet mechanism removably engaging the first and second handle members. The first handle member includes a plurality of raised thumb-grip ridges disposed on an intermediate side surface of the first handle member, and the ridges are configured to provide a frictional gripping surface.

In yet another aspect, the present invention includes a method of using a surgical instrument. The method includes the steps of: (a) providing a surgical instrument having a handle, wherein the surgical instrument handle includes a thumb ring member pivotably connected to a finger ring member, a ratchet-toothed arm fixed in and projecting generally distally from the thumb ring member, an L-shaped pawl member pivotably mounted to the finger ring member and having a first end portion projecting generally proximally from the finger ring member, and a cam lever that is pivotably connected to the finger ring member and that includes an operative contact with a second end portion of the pawl member wherein the first end portion of the pawl member is spring-biased by a spring into engagement with the ratchet-toothed arm when the cam lever is at a default first angle relative to the finger ring member; (b) pivoting the cam lever to a second angle relative to the finger ring member, such that the operative contact is sufficient to pivot the pawl member so as to overcome the spring bias and to release the engagement of the first end portion of the pawl member with the ratchet-toothed arm.

In still another aspect, the present invention includes a surgical instrument having a handle ratchet mechanism with a single-button release/defeat feature, wherein the handle ratchet mechanism includes a first engagement member, a second engagement member pivotably mounted to a handle portion and projecting toward the first engagement member (with a first end portion of the second engagement member being biased into engagement with the first engagement member), and a cam button pivotably connected to the handle portion and comprising an operative contact with a second end portion of the second engagement member. The mechanism is configured such that when the cam button is at a first angle relative to the second engagement member, the operative contact is sufficient to pivot the second engagement member so as to overcome the biased engagement of the second engagement member with the first engagement member, and, when the cam button is at a second angle relative to the second engagement member, the operative contact is sufficient to pivot the second engagement member so as to overcome the biased engagement of the second engagement member with the first engagement member and is sufficient to bias the second engagement member out of engagement with the first engagement member.

In another aspect, the present invention includes a surgical instrument having a handle operatively connected to an elongate shaft. The handle includes a thumb ring member pivotably connected to a finger ring member, a toothed first engagement member comprised by the thumb ring member, a second engagement member pivotably mounted in the finger ring member, a first end portion of the second engagement member being biased into engagement with the toothed first engagement member, and an elongate cam member movably connected to the finger ring member. The cam member includes an operative contact with a second end portion of the second engagement member. The handle is configured such that when the elongate cam member is in a first position relative to the second engagement member, the operative contact is sufficient to move the second engagement member such that the operative contact provides a force sufficient to overcome the biased engagement of the second engagement member with the toothed first engagement member, and, when the elongate cam member is in a second position relative to the second engagement member, the operative contact is sufficient to move the second engagement member so as to overcome the biased engagement of the second engagement member with the first engagement member and is sufficient to bias the second engagement member out of engagement with the first engagement member.

BRIEF DESCRIPTION OF THE DRAWINGS

FIGS. 2C-2E depict, respectively, engaged, released, and defeated ratchet states for the first handle embodiment in longitudinal section along line 2-2 of FIG. 2;

FIGS. 2F-2G show alternative user grip positions useful with handle embodiments of the present invention;

FIGS. 5-5A illustrate an in-line/traditional convertible embodiment of a handle;

FIGS. 10A-10C illustrate a handle housing a sixth ratchet mechanism embodiment;

FIGS. 12A-12C illustrate a handle housing a eighth ratchet mechanism embodiment;

FIGS. 13A-13C depict a handle housing a ninth ratchet mechanism embodiment;

FIGS. 15A-15C depict a handle housing a eleventh ratchet mechanism embodiment;

FIGS. 17A-17C illustrate a handle housing a thirteenth ratchet mechanism embodiment;

DETAILED DESCRIPTION

Figure 1:
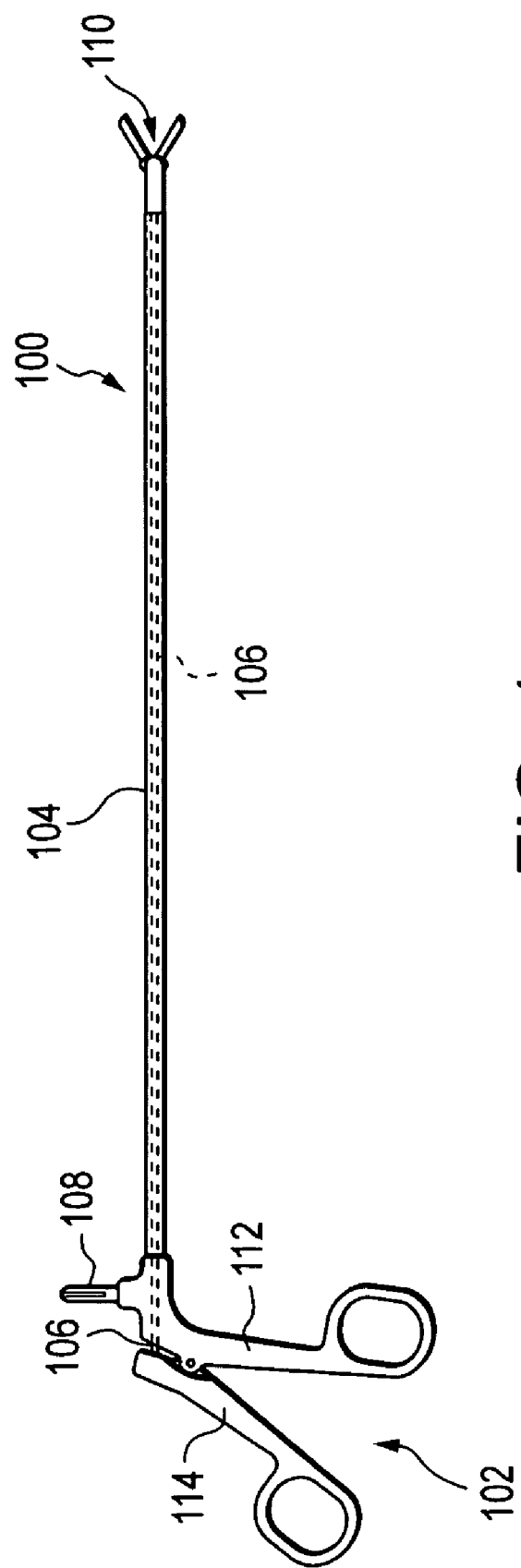
FIG. 1 is a prior art laparoscopic tool device.

A first embodiment of a handle 202 for a laparoscopy device 200 is illustrated with reference to FIGS. 2-2E. The handle 202 includes a thumb ring member 204 pivotably attached at a pivot pin 208 to a finger ring member 206. The thumb and finger ring members 204, 206 preferably are constructed of a resin material but may alternatively be constructed of plastic, or other materials known in the art to be suitable for multiple sterilizations in an autoclave. A single-use embodiment may be constructed of materials known in the art, but not necessarily configured for multiple sterilizations. An elongate tubular shaft 280 extends distally from the finger ring member 206. An actuation rod 282 extends distally from the thumb ring member 204 through the shaft 280. At the distal end of the device 200, an end effector 284 is operably connected both to the shaft 280 and the actuation rod 282.

In the preferred embodiment illustrated, a ratchet mechanism 230, embodied as a single-button release/defeat ratchet mechanism, is mounted in the handle 202 and configured to selectably secure the thumb ring member 204 at a user-selected angle to the finger ring member 206. Alternative embodiments may not include a ratchet mechanism; but, in a preferred aspect of those alternative embodiments, the space occupied by the ratchet mechanism within the handle 202 preferably is filled by a metal insert or other appropriate material to maintain the balance and tactile properties associated with embodiments including a ratchet mechanism In the illustrated embodiment of FIGS. 2-2E, a thumb aperture 205 of the thumb ring member 204 includes an optional soft ring insert 210. A similar insert optionally may be provided in the finger ring member 206, either with or without the thumb ring insert. The soft ring insert 210 preferably is formed from a pliable, non-latex material and can provide different advantages including, for example: enhanced frictional surface for improved grip; softer contact surface to provide ergonomic comfort, particularly in extended use conditions; and, improved purchase/security for a user with smaller hands.

Figure 2:
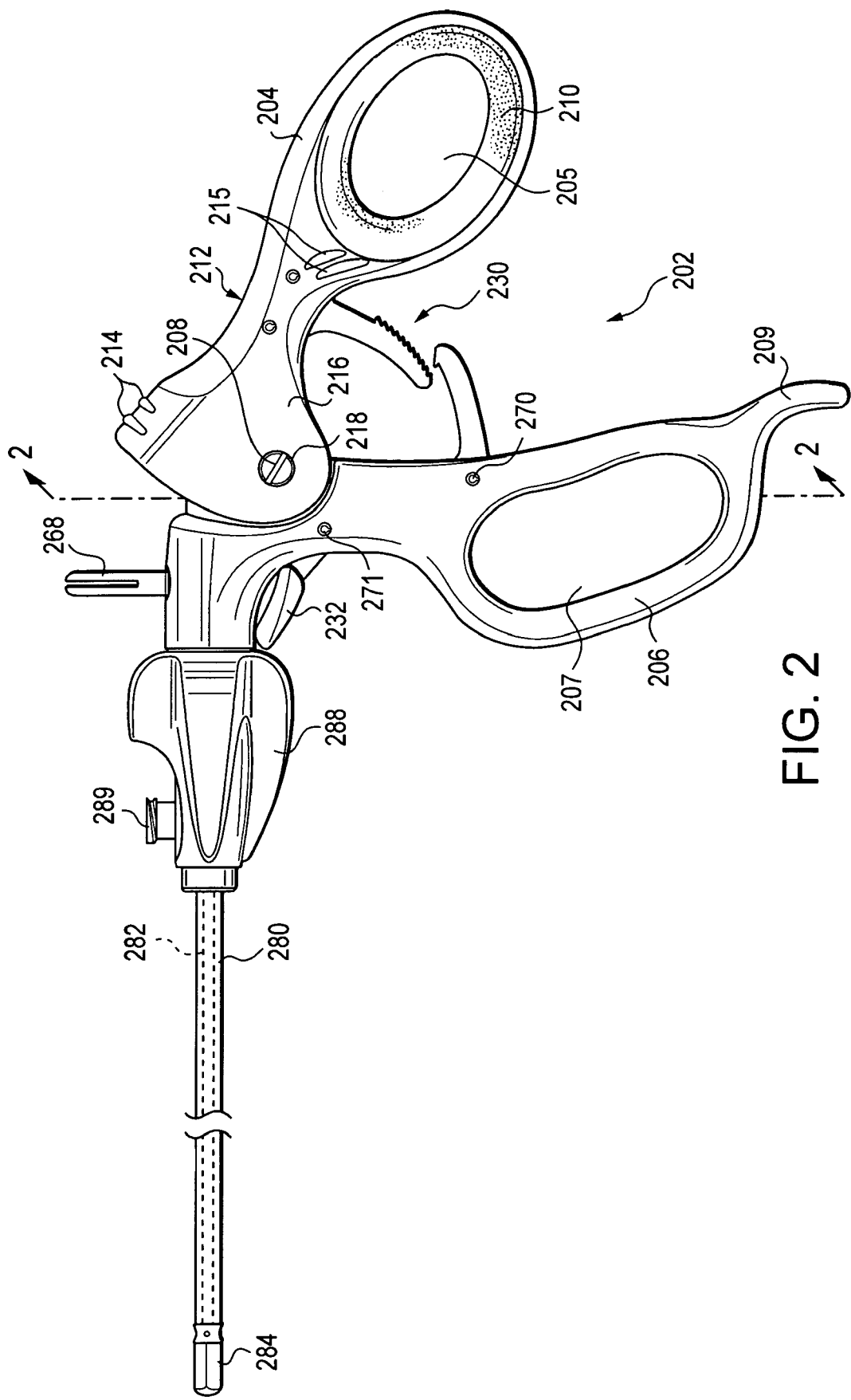
FIG. 2 illustrates a laparoscopic device incorporating a first handle embodiment of the present invention.
Figure 2A:
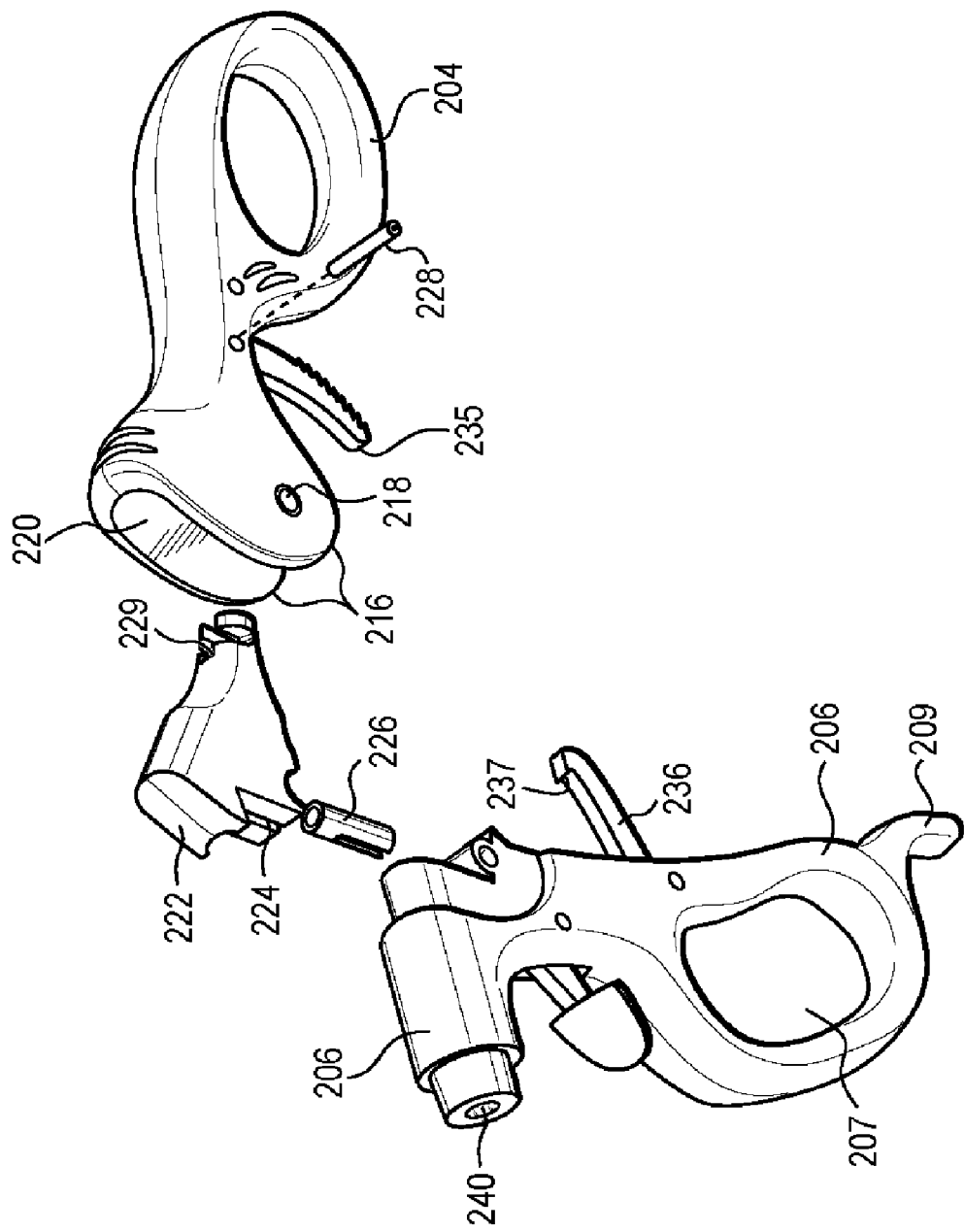
FIG. 2A is a partially exploded view of the first handle embodiment.
Figure 2B:
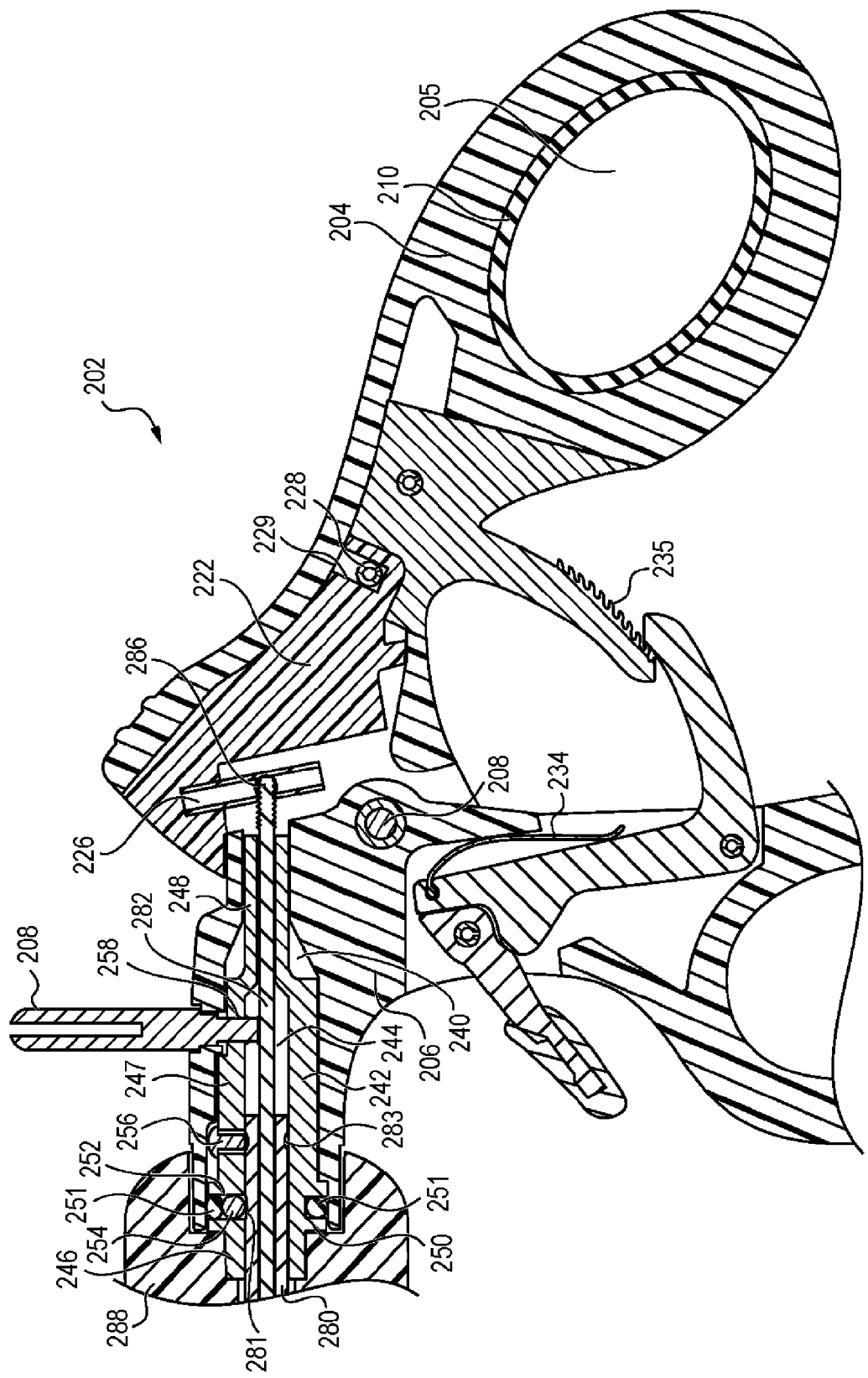
FIG. 2B is a longitudinal sectional view of the first handle embodiment along line 2-2 of FIG. 2, illustrating a bearing assembly.
Figure 2C:
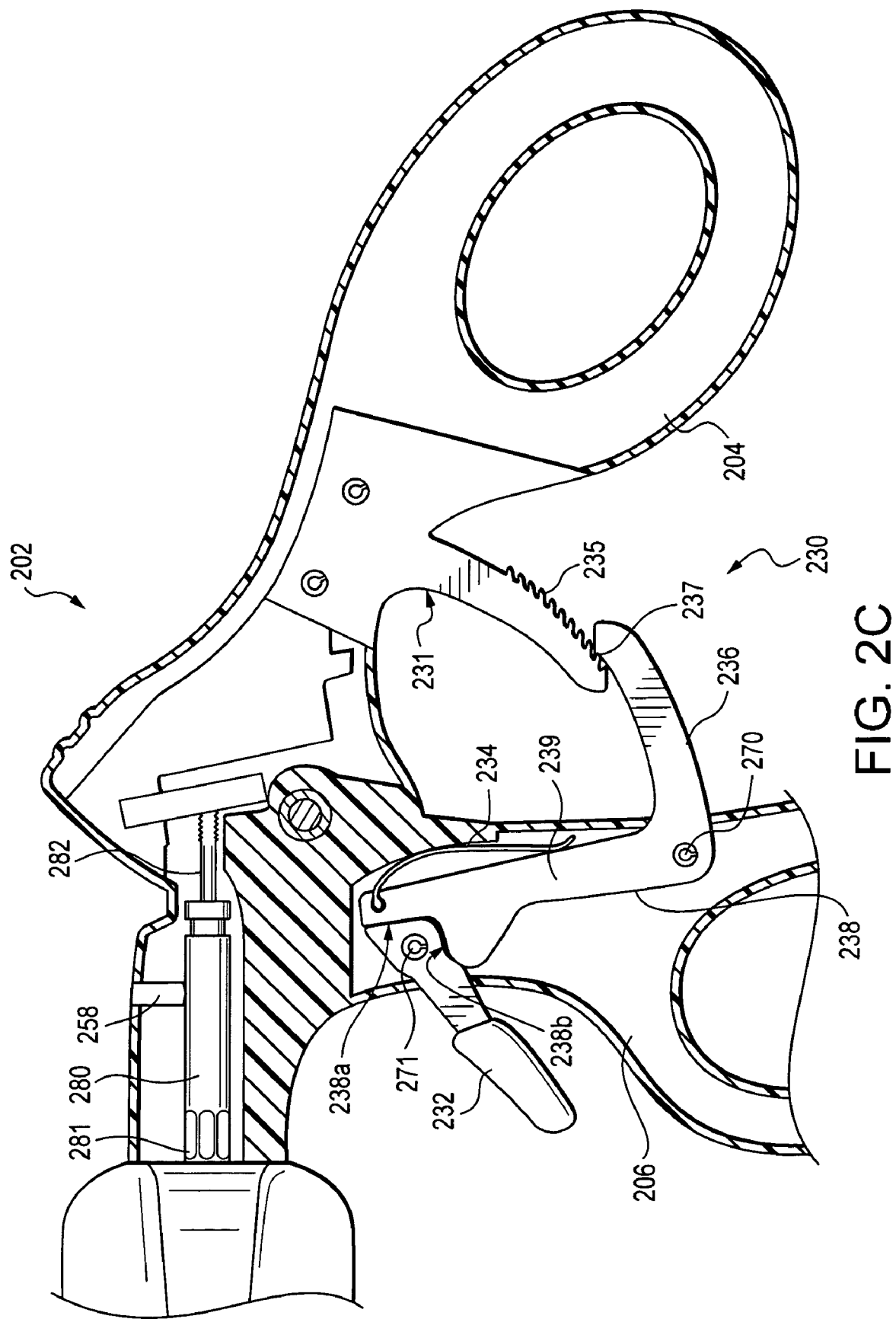
Figure 2D:
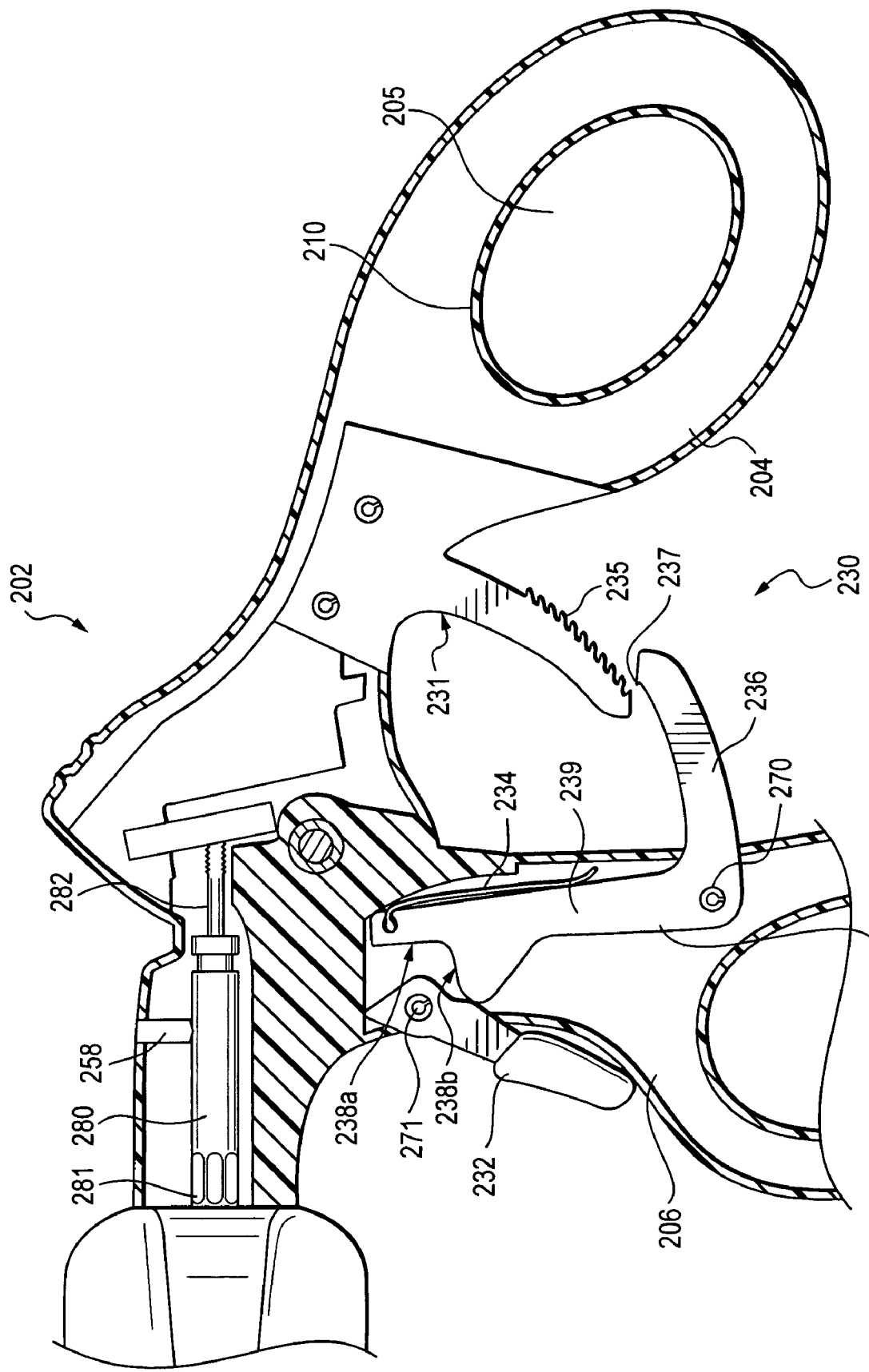
Figure 2G:
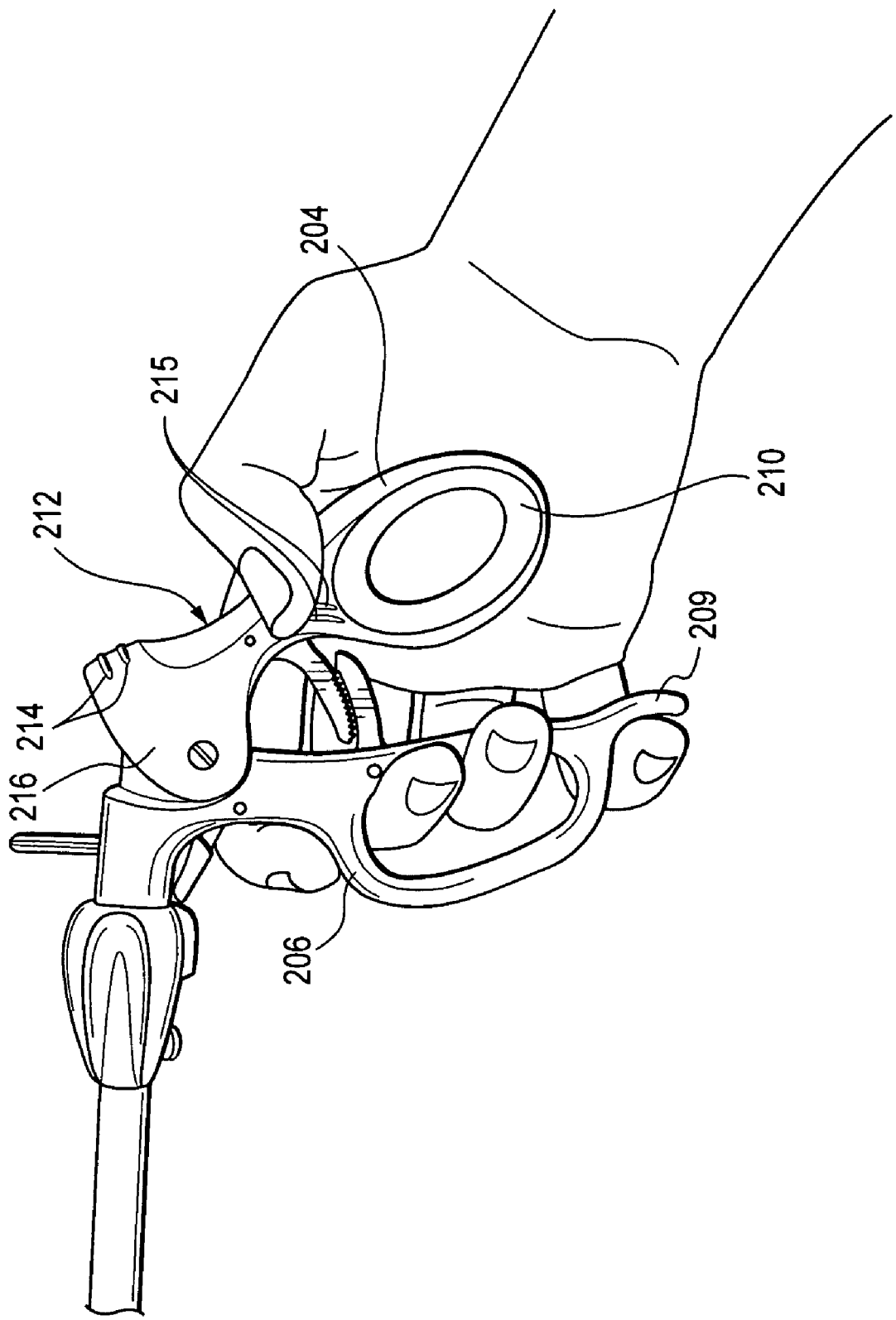

As is illustrated in FIGS. 2F and 2G, the proximal surface 212 of the thumb ring member 204 preferably bows inward/distally above the thumb aperture 205 in a manner that allows a user comfortably to operate the thumb ring member 204 in a "palm grip" rather than the traditional or "precision grip" (not shown) where the thumb is extended at least partially through the thumb aperture 205. In a preferred embodiment, a textured surface (e.g., grooves or ridges) on an upper proximal surface and/or on an intermediate side surface of the thumb ring member provides both enhanced frictional contact and a tactile cue for use in the "thumb-up palmed position" (see, e.g., proximal surface ridges 214 in FIG. 2F) and in the "thumb-down palmed position" (see, e.g., intermediate side ridges 215 in FIG. 2G). Preferred embodiments of the handle 202 also may include other ergonomic design features. For example, the finger ring aperture 207 may be sized to accommodate the middle two fingers of a user's hand while the user's index finger can be used for actuation of the ratchet mechanism above the finger ring 206, and the user's little finger can be contact the pinky rest 209. In preferred embodiments, the surfaces of the finger ring aperture 207 and the thumb ring aperture 205 are contoured to provide comfort during use with either of a user's hand, and also to facilitate a user removing her hands from gripping the handle 202. As another example, the handle 202 preferably is oriented at an angle relative to the shaft 280 that provides for ease of use with either of a user's hands as well as in an "upside-down" grip.

FIG. 2A shows a partially exploded view of the handle 202, and FIG. 2B shows a cross-sectional view of the handle 202. The forward upper region of the thumb ring member 204 is constructed to engage the finger ring member 206. Specifically, the forward upper region includes two distally extending arms 216 with a pivot aperture 218 through each arm for engaging the pivot pin 208 on either side of an upper rear region of the finger handle member 206. The rear upper region of the thumb ring member 204 includes a receiving chamber 220 configured to receive an actuation rod retainer 222. When assembled to the thumb ring member 204, the actuation rod retainer 222 preferably is held in place by a ratchet-retainer pin 228 engaging a mounting groove 229 (see FIG. 2A). The actuation rod retainer 222 preferably is a molded piece having a keyhole groove 224 dimensioned to receive and retain a ball 286 (or other shaped rod-retaining structure) on the proximal end of the actuation rod 282. Most preferably, the groove 224 includes a semi-cylindrical metal insert 226 that maintains contact with the ball 286. The open side of the groove 224 and the open side of the metal insert 226 are aligned to form a retaining channel. The metal insert 226 provides a durable interface between the ball 286 of the actuation rod 282 and the thumb ring member 204 used to actuate the rod in axial motion. The construction described for the retainer 222 provides for insulation of a user from electric current flowing through the actuation rod 282. In addition, the described construction provides for ease of manufacture as the components of the thumb ring member 204 may be assembled together before being connected to the finger ring member 206. In an alternative embodiment, the actuation rod retainer may be formed as a single metallic component with a key-lock groove to capture the proximal ball of the actuation rod. In preferred embodiments and as illustrated, all handle components are constructed and dimensioned such that, once the electrode is connected to an electrosurgical power unit, all electroconductive components are insulated from being touched by a user.

In the illustrated embodiment of FIGS. 2-2E, the finger ring member 206 includes an elongate finger aperture 207 (e.g., such as appropriate for inserting more than one finger) with a pinky-rest 209 extending downward therefrom. The finger aperture 207 and pinky rest 209 preferably are oriented at an angle that provides comfort and ergonomic advantage for a user whether the thumb ring member 204 is being used in a "palm grip" or in a "precision/thumb-grip" application (see FIGS. 2F-2G). The upper region of the finger ring member 206 includes a channel 240 extending along its proximal-distal axis. A bearing 242 is disposed in the channel 240.

The bearing 242 is generally cylindrical, and has a lumen 244 extending through its central longitudinal axis, through which a proximal portion of the actuation rod 282 extends. The bearing 242 has a slightly smaller outer diameter distal portion 246, an intermediate body portion 247, and a significantly smaller outer diameter proximal portion 248. A longitudinally grooved proximal region 281 of the device shaft 280 extends rotatably into the distal part of the lumen 244. Near the distal end of the intermediate body portion 247, a groove 250 encircles the diameter of the bearing 242. A detent ball-holding aperture 252 extends between the groove 250 and the bearing lumen 244. An o-ring 251 in the groove 250 retains a ball detent 254 in the aperture 252 and biases it against the longitudinal grooves (not shown) in the proximal region 281 of the shaft 280. This detent provides for indexed rotatability of the shaft 280. Specifically, the shaft 280 may be rotated about its longitudinal axis in discrete increments wherein each increment of rotation provides for engagement of the ball detent 254 with a longitudinal groove. Near the middle of the bearing's intermediate body portion 247, a set screw 256 is mounted through the wall of the bearing 242. The set screw 256 engages a circumferential retention groove 283 adjacent the proximal end of the shaft 280 in a manner that allows the shaft to rotate about its longitudinal axis relative to the bearing 242, but axially retains the shaft within the bearing and thereby in the handle 202. Near the proximal end of the intermediate body portion 247, the upper surface of the bearing 242 is slightly flattened and an electrode aperture 258 is open to the lumen 244. An electrode 268 configured for connection to an electrosurgical power unit extends through the aperture 258 and contacts the actuation rod 282 in a manner providing for current flow to the rod, but still allowing it to rotate.

The proximal body portion 248 of the bearing 242 extends nearly to a proximal end surface of the finger ring member 206 and helps to secure the bearing 242 in the channel 240. In addition to providing the structural components described above, the bearing 242 provides for efficient assembly of the device 200 by allowing ease of assembly of components into the finger ring member 206. The bearing 242 preferably is formed from a metal or plastic material and, in a preferred embodiment, provides electrical insulation around the shaft 280.

An indexed rotation knob 288 rotatably overlaps the distal exterior of the upper region of the finger ring member 206 and is attached to the exterior of the shaft 280. The rotation knob 288 preferably includes a flush port 289 open to the interior of the shaft 280. (See, e.g., U.S. Pat. No. 5,489,290, which is incorporated herein by reference, for illustration of a representative flush port/rotation knob mechanism). The rotation knob 288 provides means for rotating the shaft 280 about its longitudinal axis, relative to the handle 202. The knob 288 preferably is disposed in an ergonomically-oriented, position such that a user may rotate it with an index finger without removing or altering her grip on the handle 202, and its outer surface preferably includes a plurality of broad grooves to provide purchase for the user's index finger. As described above, the rotation of the shaft by rotating the knob 288 is indexed (by the interaction of the ball detent 254 with longitudinal grooves on the shaft 280) to allow precise, controlled rotation of the shaft 280.

The handle 202 includes a ratchet mechanism 230, described with reference to FIGS. 2C-2E, the design of which provides advantages for assembly of the device 200 and ease of use. The ratchet mechanism 230 preferably includes a four-piece design. A ratchet-toothed member 231 is fixed in the thumb ring member 204. A release/defeat button, shown here as a cam member 232, an L-shaped pawl member 238, and a leaf spring 234 are disposed in the finger ring member 206. The ratchet-toothed member 231 includes a curved, toothed projection 235 that extends generally distally out of the thumb ring member 204 toward the finger ring member 206. The pawl member 238 includes a curved pawl projection 236 that extends proximally out of the finger ring member 206 toward the thumb ring member 204 and that has a pawl tooth 237 on its upper surface. The pawl member 238 also includes a first cam-engaging surface 238a on the distal side near the upper end of its vertical pawl leg 239 and a second cam-engaging surface 238b projecting distally below the first cam-engaging surface 238a. The upper end of the leaf spring 234 is secured near the upper end of the pawl member 238 and its bowed-out surface contacts an interior surface of the finger ring member 206, thereby biasing the vertical pawl leg 239 in a distal direction. The pawl member 238 is pivotably attached within the finger ring member 206 by a pawl pivot pin 270, which is located proximate the juncture of the curved pawl projection 236 with the vertical member 239. The cam member 232 is pivotably attached to the finger ring member 206 by a cam pivot pin 271. In an alternative embodiment, the distal projection of the thumb ring member may include one or more pawl teeth, and the proximal projection of the finger ring member may include a ratcheted surface. This reversibility of the complementary/engaging surfaces is also applicable to other embodiments of the present invention.

The ratchet mechanism 230 can be actuated to one of three user-selected states (engaged, released, and defeated), which are described, respectively, with reference to FIGS. 2C, 2D, and 2E.

As shown in FIG. 2C, when the ratchet mechanism 230 is in an engaged state, the pawl tooth 237 of the pawl member 238 engages the teeth of the curved, toothed projection 235. This engagement prevents the thumb ring 204 from being moved proximally relative to (i.e., away from) the finger ring 206, but allows it to be moved distally relative to (i.e., closer to) the finger ring. In the engaged state, the position of the pawl member 238 is maintained by the bias of the leaf spring 234 against an inner surface of the finger ring member 206. This bias exerts a distal/downward force against the vertical pawl leg 239, thereby pivoting the pawl member 238 about the pawl pivot pin 270 such that the pawl toothed projection 236 is directed distally/upward into engagement with the curved, toothed projection 235 of the thumb ring member. In the engaged position, the cam member 232 is at rest and does not have significant force-exerting contact with the pawl member 238.

As shown in FIG. 2D, when the ratchet mechanism 230 is in a released state, the pawl tooth 237 of the pawl member 238 is disengaged from the teeth of the curved, toothed projection 235. This disengagement allows the thumb ring 204 to be moved toward or away from the finger ring 206. The disengagement of the released state is effected by holding the cam member 232 in a downward position. In the released state, a proximal portion of the cam member 232 is dynamically held against the second cam-engaging surface 238b of the pawl member 238. This contact forces the vertical pawl leg 239 proximally, against the bias of the leaf spring 234. This proximal force pivots the pawl member 238 about the pawl pivot pin 270 such that the pawl toothed projection 236 is levered distally/downward and out of engagement with the curved, toothed projection 235 of the thumb ring member. To resist the bias of the leaf spring 234, the cam member 232 must be held in position to maintain the released state.

As shown in FIG. 2E, when the ratchet mechanism 230 is in a defeated state, the pawl tooth 237 of the pawl member 238 is disengaged from the teeth of the curved, toothed projection 235. This disengagement allows the thumb ring 204 freely to be moved toward or away from the finger ring 206. The disengagement of the released state is effected by moving the cam member 232 into an upward position. In the defeated state, a proximal portion of the cam member 232 is locked against the first cam-engaging surface 238a of the pawl member 238. This contact forces the vertical pawl leg 239 proximally, against the bias of the leaf spring 234. The proximal force pivots the pawl member 238 about the pawl pivot pin 270 such that the pawl toothed projection 236 is directed distally/downward and out of engagement with the curved, toothed projection 235 of the thumb ring member. The cam member 232 is rotated past a point of inflection such that the cam member 232 angle of contact with the first cam-engaging surface 238a locks the cam member 232 in the upward position to maintain the defeated state. In an alternative embodiment (not shown), a leaf spring may be provided between the thumb ring member 204 and finger ring member 206 to bias them apart (in an "open" position).

Figure 3A:
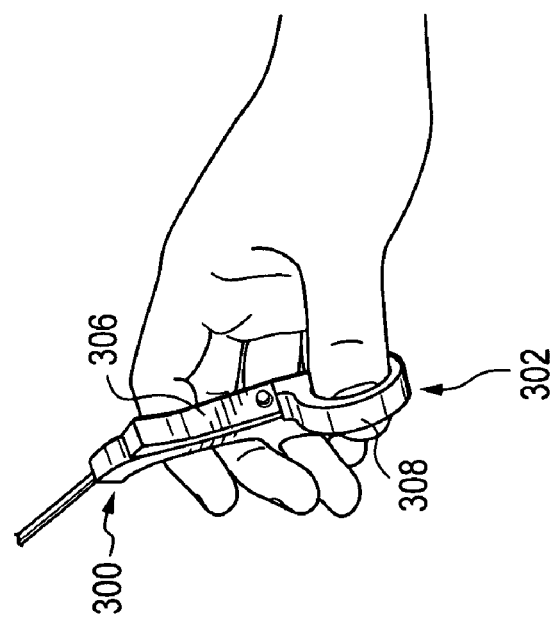
FIGS. 3-3A illustrate a first thumb-twist embodiment of a handle.
Figure 3:
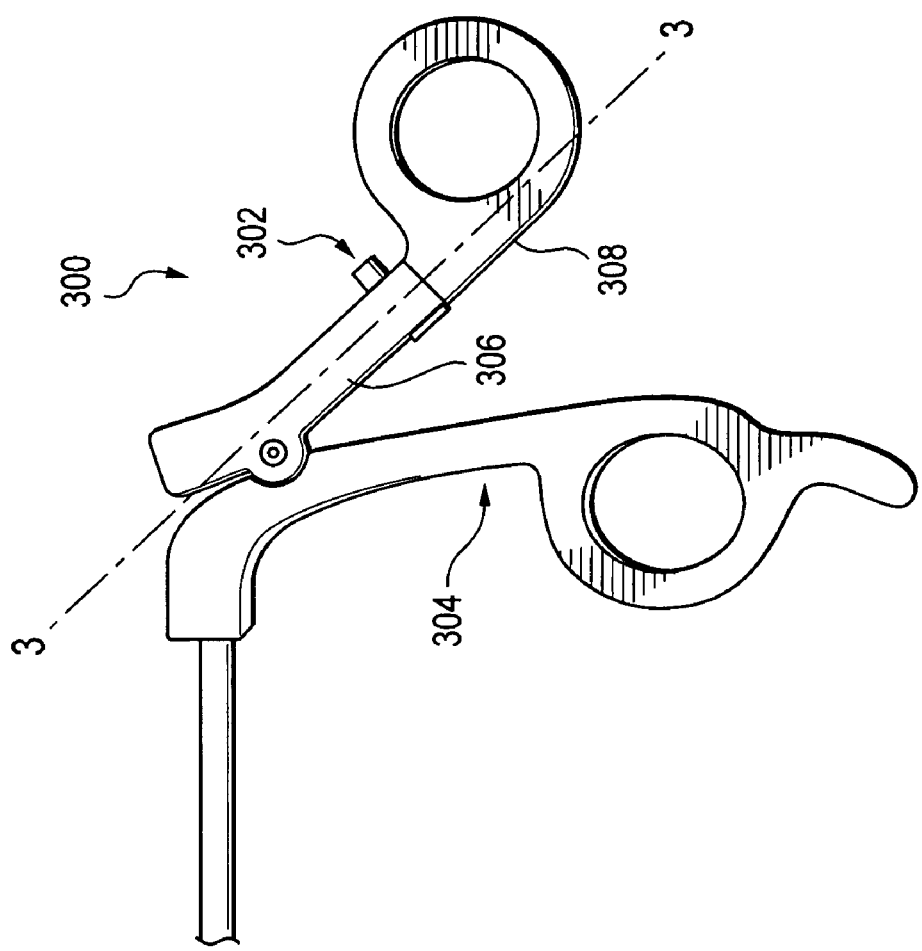

A first thumb-twist handle embodiment 300 is shown in FIGS. 3A-3B. The handle 300 includes a thumb ring member 302 and a finger ring member 304. The thumb ring member 302 includes a pivot arm component 306 that is pivotably connected to the finger ring member 304 in a manner allowing the thumb ring member to pivot within the same plane as the finger ring member 304 in the same fashion as a typical handle design. The thumb ring member 302 includes a thumb aperture component 308 that is pivotably connected to the pivot arm component 306 in a manner that allows the thumb aperture component 308 to pivot relative to the pivot arm component 306 about the longitudinal axis (line 3-3) of the pivot arm component 306 (i.e., the proximal portion of the thumb aperture component 308 can rotate out of a major plane defined by the default orientation of the thumb ring member 302 and finger ring member 304 in FIG. 3A). This design feature allows a user to maintain a natural thumb-wrist orientation while allowing a greater range of handle movement without disengaging the user's thumb from the handle 300.

Figure 4A:
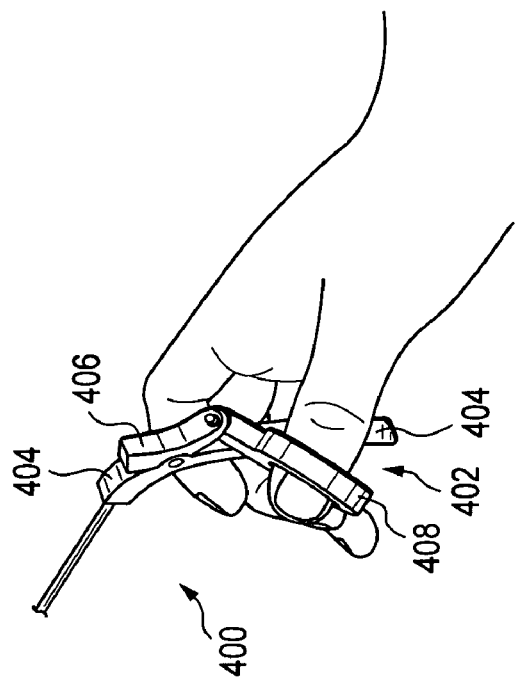
FIGS. 4-4A illustrate a second thumb-twist embodiment of a handle.
Figure 4:
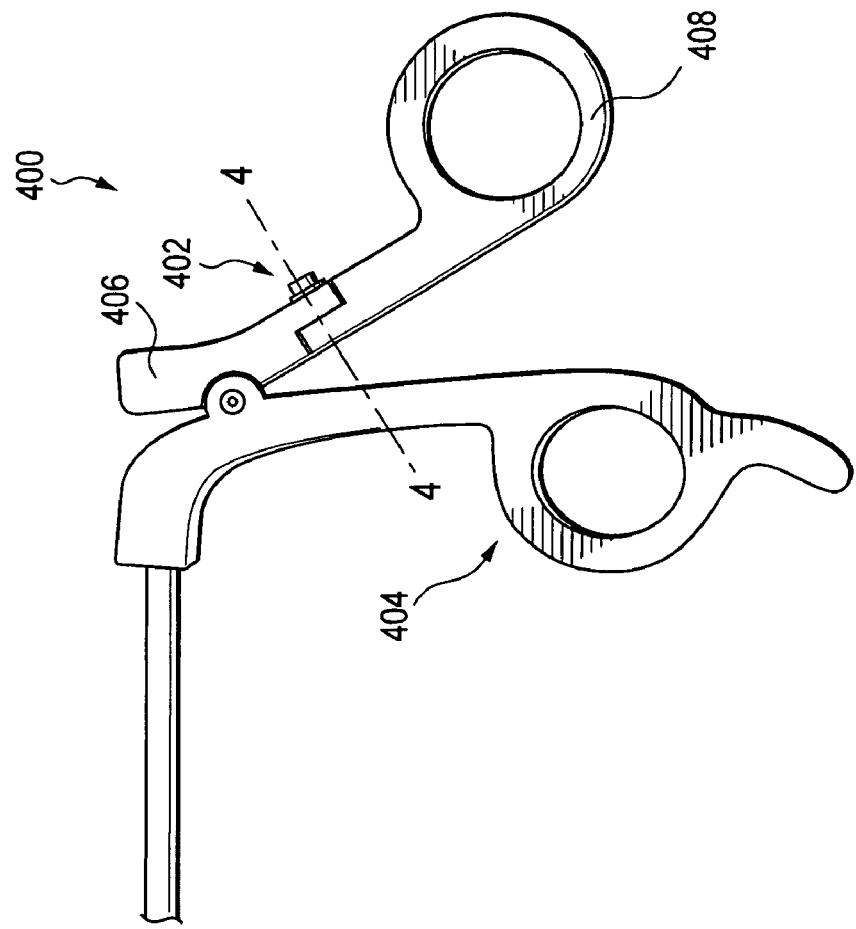

A second thumb-twist handle embodiment 400 is shown in FIGS. 4A-4B. The handle 400 includes a thumb ring member 402 and a finger ring member 404. The thumb ring member 402 includes a pivot arm component 406 that is pivotably connected to the finger ring member 404 in a manner allowing the thumb ring member to pivot within the same plane as the finger ring member 404 in the same fashion as a typical handle design. The thumb ring member 402 includes a thumb aperture component 408 that is pivotably connected to the pivot arm component 406 in a manner that allows the thumb aperture component 408 to pivot out of the longitudinal axis of the pivot arm component 406 (i.e., the entire thumb aperture component 408 can rotate along a transverse axis 4-4 and out of a major plane defined by the default orientation of the thumb ring member 402 and finger ring member 404 in FIG. 4A). This design feature allows a user to maintain a natural thumb-wrist orientation while allowing a greater range of handle movement without disengaging the user's thumb from the handle 400.

A first in-line/traditional convertible embodiment of a handle 500 for a laparoscopic device 501 is depicted in FIGS. 5-5A. The handle 500 includes a thumb ring member 502 and a finger ring member 504. The thumb ring member 502 is pivotably connected to the finger ring member 504 in a manner allowing the thumb ring member to pivot within the same plane as the finger ring member 504 in the same fashion as a typical handle design. A pivoting mechanism 508 is disposed at the juncture of the handle 500 with a shaft 510 and other, more distal components of the device 501. This pivoting mechanism 508 provides for a user-selected ability to configure the handle 502 in a "traditional" (or "pistol-grip") orientation, wherein the longitudinal axis of the finger ring member 504 is nearly perpendicular relative to the shaft 510 (see FIG. 5). Or, the user may pivot the handle 500 upward into an "in-line" orientation, wherein the longitudinal axis of the finger ring member 504 is nearly coaxial with the longitudinal axis of the shaft 510 (see FIG. 5A). Those of skill in the art will appreciate that user may select to orient the handle 500 at a greater or lesser angle than is illustrated.

Figure 6A:
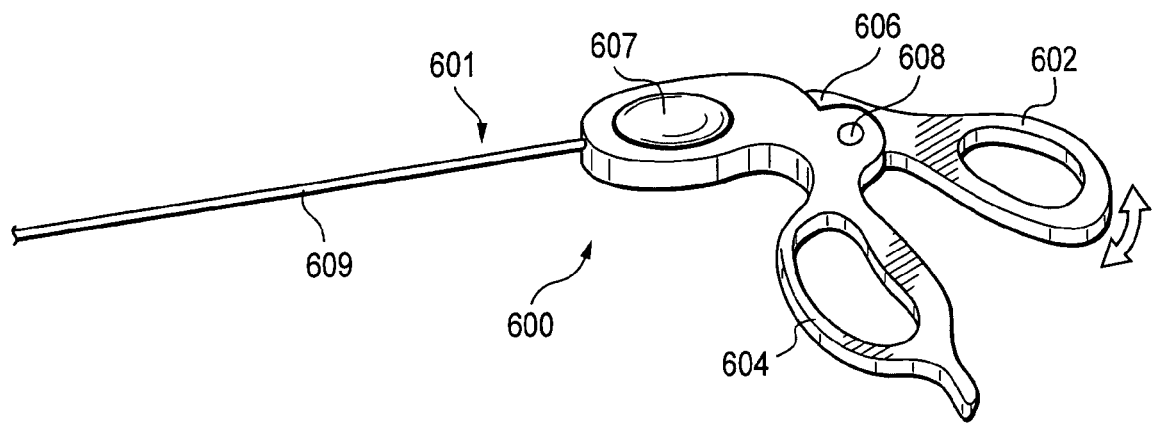
FIGS. 6A-6C depict different external configuration embodiments of a handle.
Figure 6B:
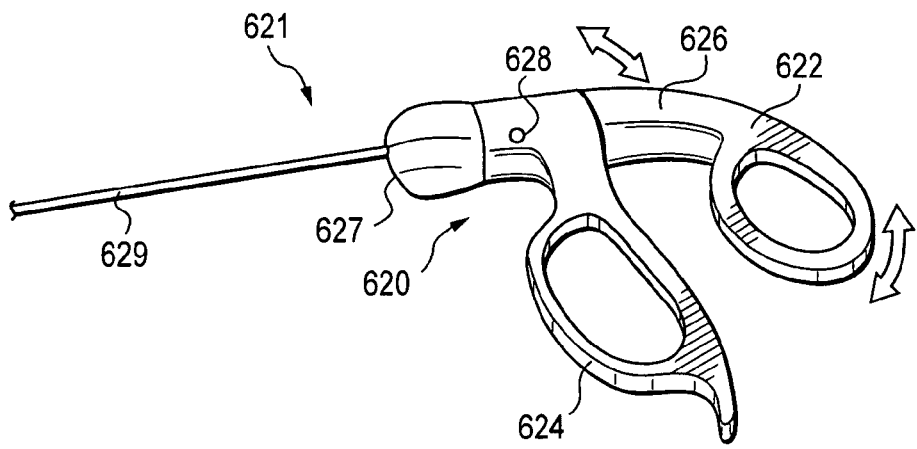
Figure 6C:
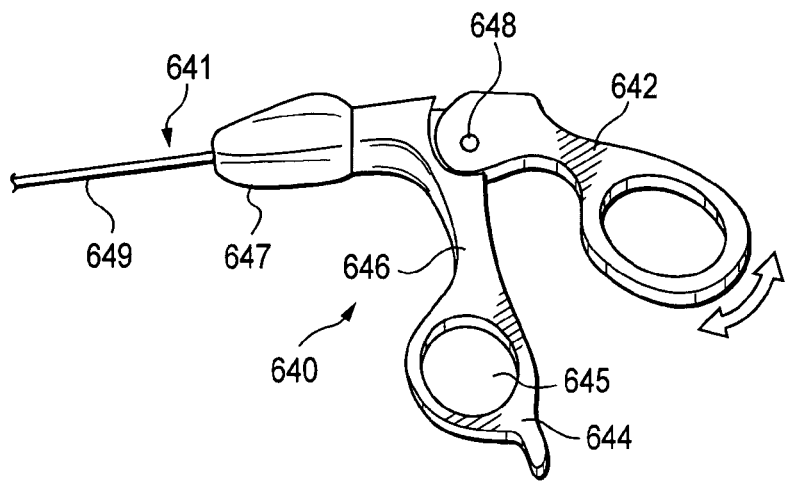

FIGS. 6A-6C illustrate alternative handle embodiments wherein the shape and relative position of the ring members and rotation knob are varied.

A first alternative geometry embodiment of a handle 600 for a laparoscopic device 601 is depicted in FIG. 6A. The handle 600 includes a thumb ring member 602 and a finger ring member 604. The thumb ring member 602 includes a pivot arm component 606 that is pivotably connected to the finger ring member 604 by a pivot pin 608 in a manner allowing the thumb ring member to pivot within the same plane as the finger ring member 604. The pivot pin 608 is disposed low and proximally on the upper region of the finger ring member 604. The portion of the thumb ring pivot arm component 606 that is above the pivot pin 608 goes into an open region in the finger ring member 604 when the handle portions are opened/separated. A rotation knob 607 for rotating a shaft 609 of the device 601 about its longitudinal axis is disposed in a forward upper region of the finger ring member 604.

A second alternative geometry embodiment of a handle 620 for a laparoscopic device 621 is depicted in FIG. 6B. The handle 620 includes a thumb ring member 622 and a finger ring member 624. The thumb ring member 622 includes a pivot arm element 626 that is pivotably connected to the finger ring member 624 by a pivot pin 628 in a manner allowing the thumb ring member to pivot within the same plane as the finger ring member 624. The pivot pin 628 is disposed distally on the upper region of the finger ring member 624. The portion of the thumb ring pivot arm component 626 that is above the pivot pin 628 rotates above the longitudinal axis of a shaft 629 of the device when the handle members 622, 624 are opened/separated. A rotation knob 627 for rotating the shaft 629 of the device 621 about its longitudinal axis is disposed distal to a forward upper region of the finger ring member 624.

A third alternative geometry embodiment of a handle 640 for a laparoscopic device 641 is depicted in FIG. 6A. The handle 640 includes a thumb ring member 642 and a finger ring member 644. The thumb ring member 642 is pivotably connected to the finger ring member 644 by a pivot pin 648 in a manner allowing the thumb ring member to pivot within the same plane as the finger ring member 644. The pivot pin 648 is disposed in substantially the same manner as the device embodiment of FIG. 2. A rotation knob 647 for rotating a shaft 649 of the device 641 about its longitudinal axis is disposed in a forward upper region of the finger ring member 644. The finger ring member 644 includes a finger aperture 645 configured for a single finger and a finger rest stem 646 configured to support one or more fingers.

A first alternatively ratcheted embodiment of a handle 702 for a laparoscopy device 700 is illustrated with reference to FIGS. 7-7C. The handle 702 includes a thumb ring member 704 pivotably attached at a pivot pin 708 to a finger ring member 706. An elongate tubular shaft 780 extends distally from the finger ring member 706.

Figure 7:
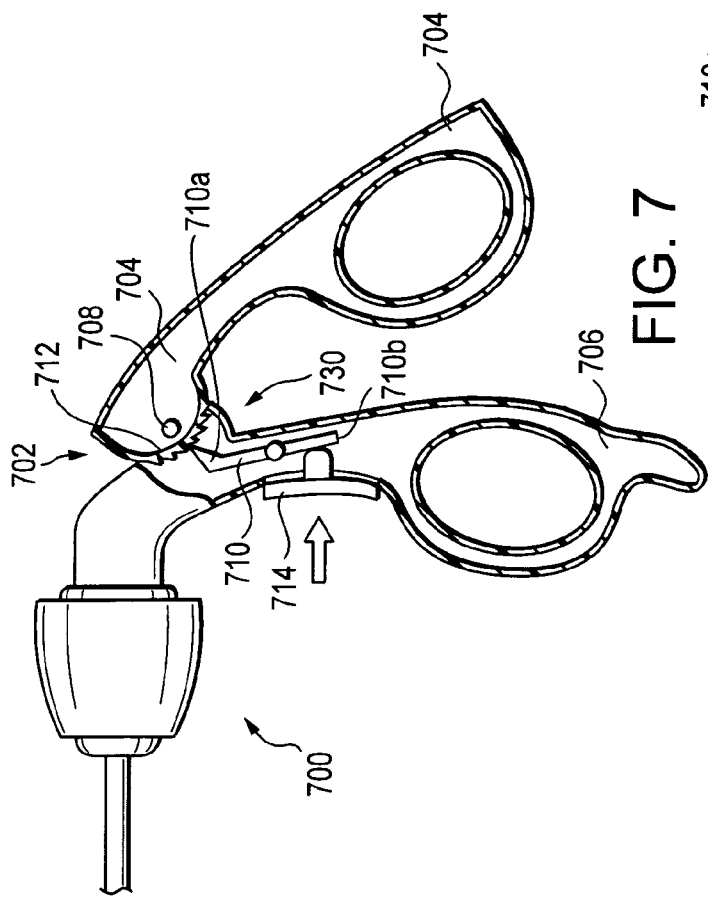
FIGS. 7-7A show a first ratchet embodiment of a handle.
Figure 7C:
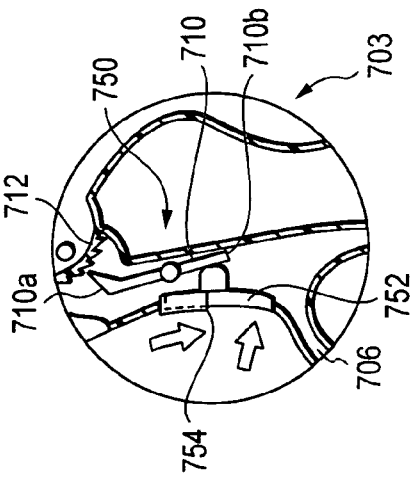
FIG. 7C illustrates a third ratchet embodiment of a handle.

In the embodiment illustrated in FIGS. 7-7C, ratchet mechanism embodiments are illustrated as comprised by a handle 702 and configured to selectably secure a thumb ring member 704 at a user-selected angle to a finger ring member 706. An upper region of the thumb ring member 704 includes a curved ratcheted surface 712 adjacent and below the pivot pin 708.

FIG. 7 depicts a first ratchet mechanism embodiment 730. In addition to the curved ratcheted surface 712, the ratchet mechanism 730 includes a cam switch 714 and a pawl lever 710. The pawl lever 710 includes an upper pawl arm 710a and a lower pawl arm 710b. The upper pawl arm 710a includes a pawl tooth 710c configured to engage the ratcheted surface 712 and the mechanism 730 includes a spring (e.g. torsion or leaf spring, not shown) that biases the pawl lever 710 into engagement with the ratcheted surface 712 when—as shown—the cam switch 714 is in a neutral position (handle-engaged state), allowing the ratchet mechanism 730 to be engaged to prevent the handle 702 from being opened. The cam switch 714 can be moved upward, exerting force against the lower pawl arm 710b to lever the pawl 710 out of engagement with the ratcheted surface 712 (handle-released state). Alternatively, the cam switch 712 may be configured to be pulled proximally into the finger ring member 706.

Figure 7A:
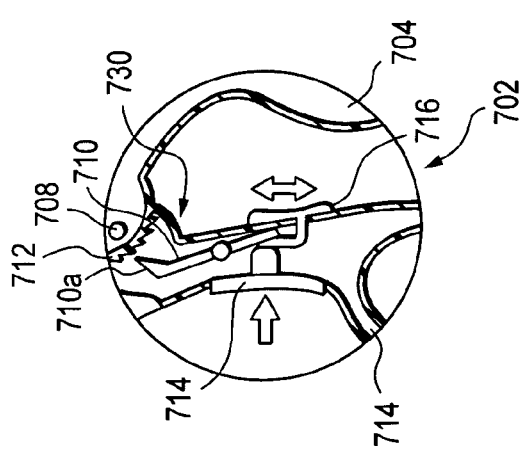

FIG. 7A illustrates a detail view of the first ratchet mechanism of FIG. 7, with the addition of a defeat switch 716. In the illustrated embodiment, the defeat switch 716 can be moved upwards to engage the lower pawl arm 710b when it (716) is disengaged from the ratcheted surface 712. When the defeat switch 716 is thus engaged, the handle 702 may freely be opened and closed.

Figure 7B:
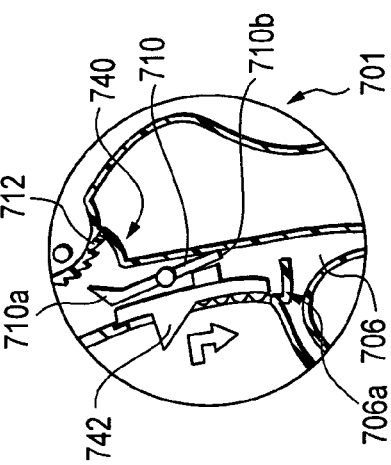
FIG. 7B illustrates a second ratchet embodiment of a handle.

FIG. 7B illustrates a detail of a second ratchet mechanism embodiment 740 in a handle 701 that is nearly identical to the handle 702 in FIG. 7, but for a different camming member arrangement. The second ratchet mechanism embodiment 740 includes a cam slide 742. In a ratchet-engaged (neutral) state, the cam slide 742 has little or no contact with the lower portion 710b of the pawl lever 710. To release the pawl lever 710 from engagement with the ratcheted surface 712, a user depresses the cam slide 742, thereby levering the upper pawl arm 710a away from the ratcheted surface 712. To defeat the engagement, a user depresses the cam slide 742 proximally to release the engagement, then locks the cam slide 742 in place by moving it downward into engagement with a notch 706a provided on the finger ring member 706.

FIG. 7C depicts a detail view of a third ratchet mechanism embodiment 750 in a handle 703 that is nearly identical to the handle 702 in FIG. 7, but for a different camming member arrangement. The third ratchet mechanism embodiment 740 includes a cam button 752 and a cam button locking slide 754. In a ratchet-engaged (neutral) state, the cam button 752 has only minimal contact with the lower portion of the pawl lever 710. To release the pawl lever 710 from engagement with the ratcheted surface 712, a user depresses the cam button 752 distally, thereby levering the upper pawl arm 710a away from the ratcheted surface 712 (released state). To defeat the ratchet engagement, a user depresses the cam button 752 to release the engagement, and then locks the cam button 752 in place by moving downward the cam button locking slide 754 over the cam button 752 to hold it (752) in place. The embodiments in FIGS. 7-7C, as well as FIGS. 12A-13C illustrate an alternative location for a thumb ring member-mounted ratchet-toothed surface. In these embodiments, the ratchet mechanism components are generally enclosed in the handle body or at least preferably do not extend significantly externally between the handle members. Those of skill in the art will appreciate that these embodiments may provide a user with more freedom to manipulate his hand around the finger ring member and thumb ring member in different orientations and/or grips than embodiments with projections from/between the handle members.

Figure 8A:
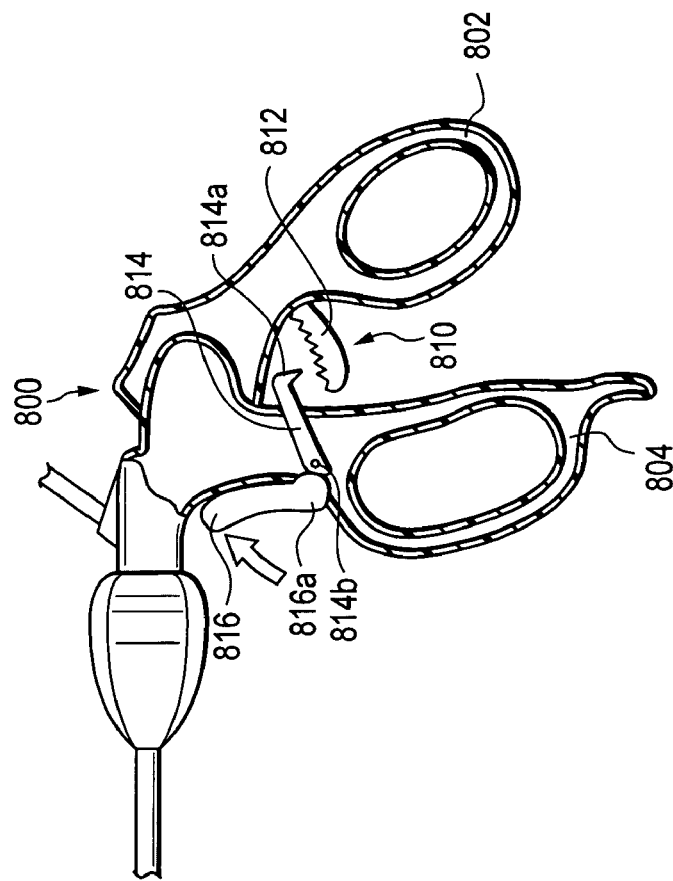
FIGS. 8A-8B depict a handle housing a fourth ratchet mechanism embodiment.
Figure 8B:
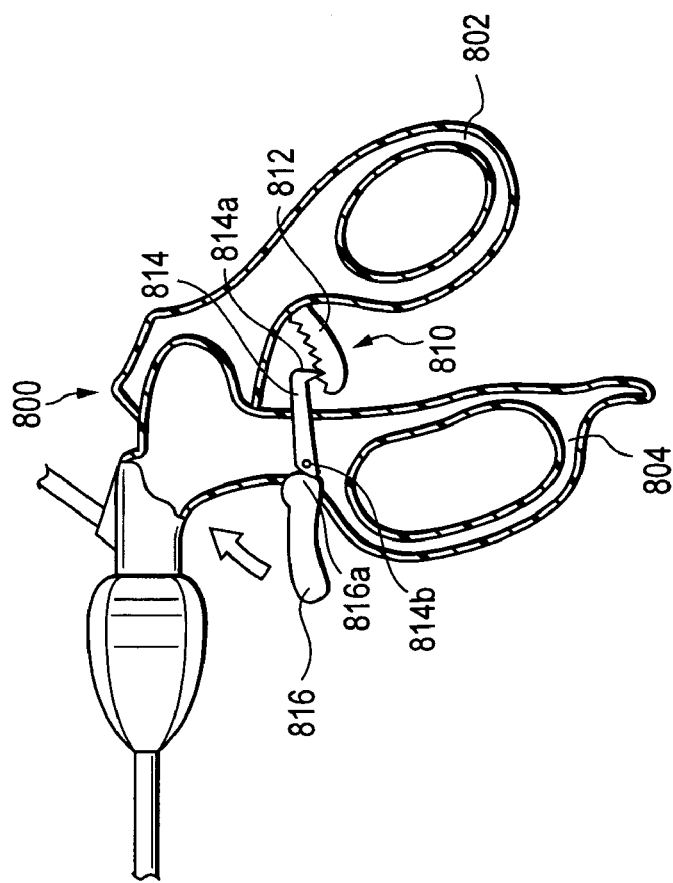

FIGS. 8A-8B illustrate a handle 800 housing a fourth embodiment of a ratchet mechanism 810. The handle includes a thumb ring member 802 pivotably attached to a finger ring member 804. The ratchet mechanism 810 includes a curved ratchet-toothed arm 812 projecting distally from the thumb ring member 802, a pawl arm 814 pivotably attached to the finger ring member 804, and a cam lever 816 pivotably connected to the finger ring member 804. A pawl-tooth 814a adjacent the proximal end of the pawl arm 814 preferably is biased into engagement with the ratchet-toothed arm 812 (e.g., by a torsion or leaf spring, not shown). A curved lower cam end 816a of the cam lever 816 contacts an angled distal end 814b of the pawl arm 814. In the neutral/engaged state illustrated in FIG. 8A, the pawl-tooth 814a is engaged with the ratchet-toothed arm 812, and the pawl arm 814 is oriented generally perpendicular to the finger ring member 804. In the ratchet-defeated state depicted in FIG. 8B, the pawl arm 814 is oriented generally parallel to the finger ring member 804, and the contact of the curved lower cam end 816a of the cam lever 816 with the angled distal end 814b of the pawl arm 814 levers the proximal pawl-tooth end 814 out of engagement from the ratchet-toothed arm 812. In the defeated state, it is preferable that the surface contact between the cam lever 816 and the pawl arm 814 be configured to form a frictional lock sufficient to resist the bias of the pawl arm toward engagement with the ratchet-toothed arm 812.

Figure 9B:
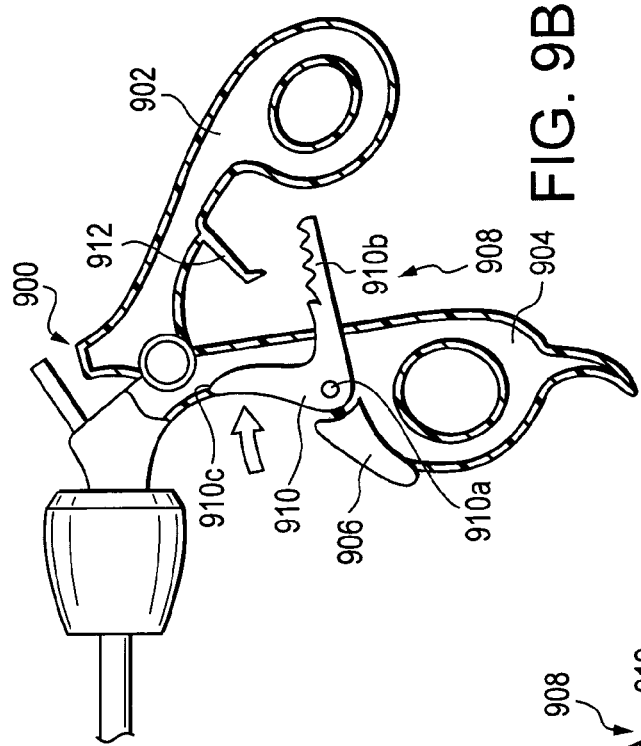
FIGS. 9A-9C show a handle housing a fifth ratchet mechanism embodiment.
Figure 9C:
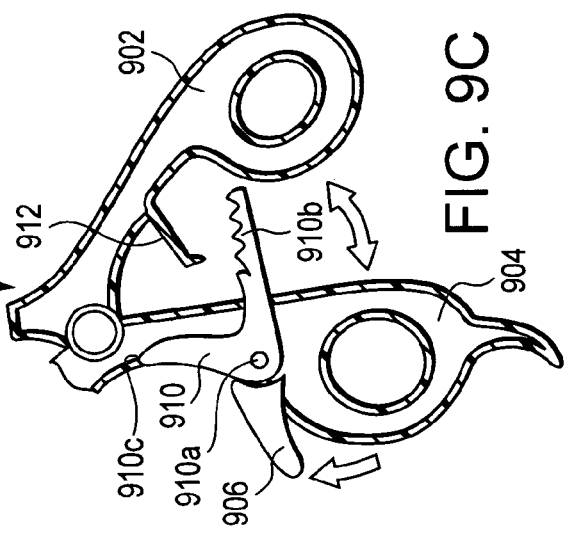
Figure 9A:
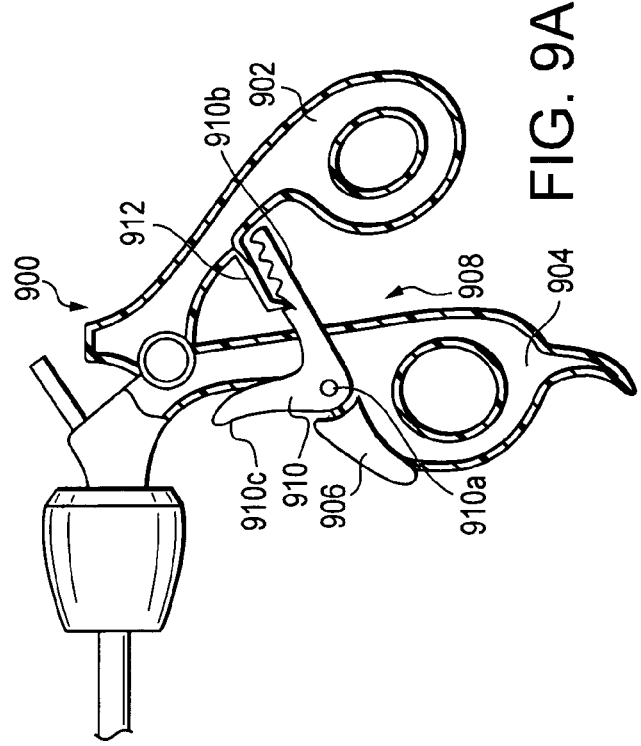

FIGS. 9A-9C illustrate a handle 900 housing a fifth embodiment of a ratchet mechanism 908. The handle includes a thumb ring member 902 pivotably attached to a finger ring member 904. The ratchet mechanism 908 includes an L-shaped member 910 having a curved ratchet-toothed arm 910b projecting generally proximally from the finger ring member 904, a lever arm 910c projecting generally distally at an acute angle from the finger ring member 904, and an over-center cam switch 906 pivotably attached to the finger ring member 904. The L-shaped member 910 includes a pivoting connection 910a to the finger ring member 904, the connection 910a being disposed at the junction of the curved ratchet-toothed arm 910b with the lever arm 910c. The ratchet mechanism 908 also includes a pawl arm 912 projecting generally distally from the thumb ring member 902. The L-shaped member 910 preferably is biased (e.g., by a torsion or leaf spring, not shown) such that the curved ratchet-toothed arm 910b engages the pawl arm 912 when the handle 900 is in a neutral state as shown in FIG. 9A. In the ratchet-released state shown in FIG. 9B, a user depresses proximally the lever arm 910c of the L-shaped member 910, thereby levering the curved ratchet-toothed arm 910b out of engagement with the pawl arm 912. In the ratchet-defeated state depicted in FIG. 9C, the L-shaped member 910 is moved to the released state shown in FIG. 9B, then the user moves upward the over-center cam switch 906 to contact the L-shaped member 910 above the pivoting connection 910a and hold it (910) in place. The over-center cam switch 906 preferably includes a mechanical locking means to maintain the released state position (e.g., an internal locking spring, a pin-groove lock, or other locking means known to those of skill in the art). In the released state, it is preferable that the surface contact between the cam lever 910c and the pawl arm 912 be sufficient to resist the bias of the pawl arm toward engagement with the ratchet-toothed arm 910b.

FIGS. 10A-10C illustrate a handle 1000 housing a sixth embodiment of a ratchet mechanism 1008. The handle includes a thumb ring member 1002 pivotably attached to a finger ring member 1004. The ratchet mechanism 1008 includes a generally arcuate member 1010 having a curved ratchet-toothed arm 1012 projecting generally proximally from the finger ring member 1004, a trigger arm 1016 projecting generally distally at an acute angle from the finger ring member 1004, and an under-center cam switch 1006 pivotably attached to the finger ring member 1004. The generally arcuate member 1010 includes a pivoting connection 1010a to the finger ring member 1004, the connection 1010a being disposed at the junction of the curved ratchet-toothed arm 1012 with the trigger arm 1016. The ratchet mechanism 1008 also includes a pawl arm 1014 projecting generally distally from the thumb ring member 1002. The generally arcuate member 1010 preferably is biased (e.g., by a torsion or leaf spring, not shown) such that the curved ratchet-toothed arm 1012 engages the pawl arm 1014 when the handle 1000 is in a neutral state as shown in FIG. 10A. In the ratchet-released state shown in FIG. 10B, a user depresses proximally the trigger arm 1016 of the generally arcuate member 1010, thereby levering the curved ratchet-toothed arm 1012 out of engagement with the pawl arm 1014. In the ratchet-defeated state depicted in FIG. 10C, the generally arcuate member 1010 is moved to the released state shown in FIG. 10B, then the user moves upward the under-center cam switch 1006 to contact the underside of the generally arcuate member 1010 below the pivoting connection 1010a to hold it (1010) in place. The under-center cam switch 1006 preferably is maintained frictionally in the released position or alternatively includes a mechanical locking means to maintain the released state position (e.g., an internal locking spring, a pin-groove lock, or other locking means known to those of skill in the art). In the released state, it is preferable that the contact between the trigger arm 1016 and the pawl arm 1014 be sufficient to resist the bias of the pawl arm toward engagement with the ratchet-toothed arm 1012.

Figure 11B:
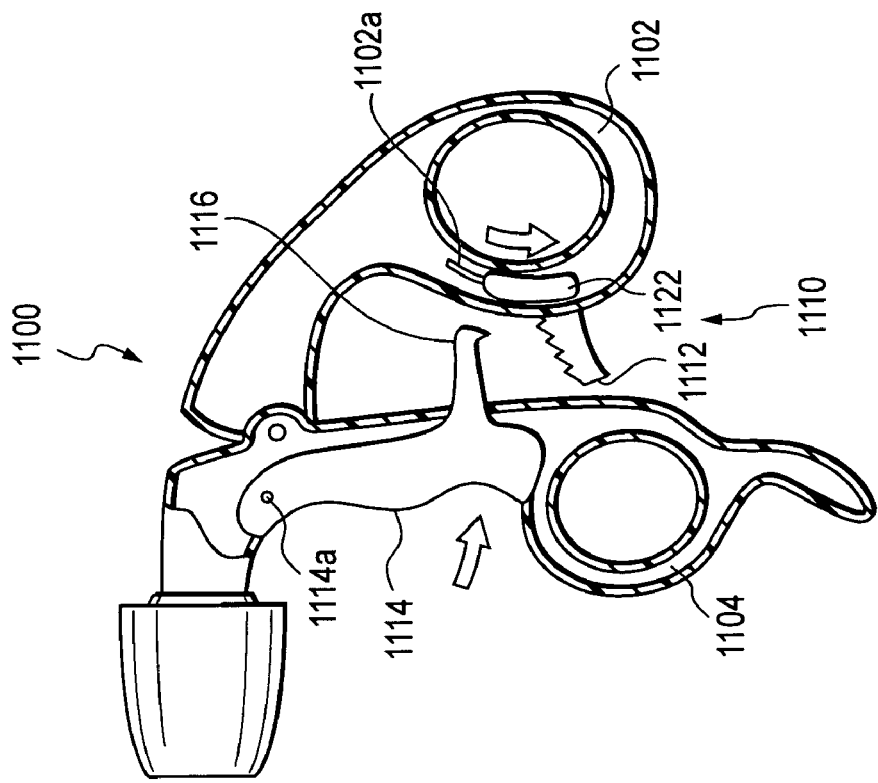
FIGS. 11A-11B depict a handle housing a seventh ratchet mechanism embodiment.
Figure 11A:
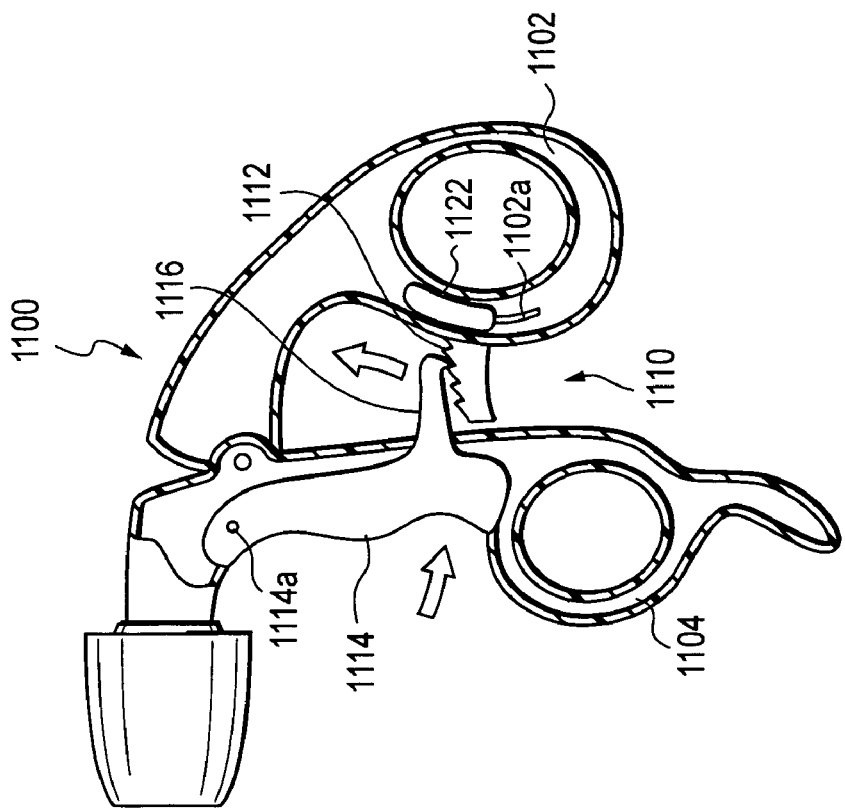

FIGS. 11A-11B illustrate a handle 1100 housing a seventh embodiment of a ratchet mechanism 1110. The handle includes a thumb ring member 1102 pivotably attached to a finger ring member 1104. The ratchet mechanism 1110 includes a curved ratchet-toothed arm 1112 projecting distally from the thumb ring member 1102 and slidably mounted therein, and a pawl grip 1114 pivotably attached at a pivot pin 1114a to the finger ring member 1104 (biased in a distal/downward position), the pawl grip 1114 including a proximally projecting pawl arm 1116. The thumb ring member 1102 includes a defeat slider button 1122 that is attached (through a groove 1102a) to the curved ratchet-toothed arm 1112, and which is configured to move the curved ratchet-toothed arm 1112 generally vertically relative to the thumb ring member 1102. In the neutral/engaged state illustrated in FIG. 11A, the pawl arm 1116 is engaged with the ratchet-toothed arm 1112, which is in an upper position relative to the groove 1102a. The ratchet mechanism 1110 may be released by a user depressing the pawl grip 1114 such that it pivots generally proximally/upward (against its bias) relative to the finger ring member 1104, which disengages the pawl arm 1116 from the ratchet-toothed arm 1112. In the ratchet-defeated state depicted in FIG. 11B, the defeat slider button 1122 is moved downward in the groove 1102a, defeating the engagement of the ratchet-toothed arm 1112 with the pawl arm 1116.

FIGS. 12A-12C illustrate a handle 1200 housing an eighth embodiment of a ratchet mechanism 1210, which is a substantially internal mechanism. The handle 1200 includes a thumb ring member 1202 pivotably attached to a finger ring member 1204. The ratchet mechanism 1208 includes a slidably disposed cam button 1212, a pivotably disposed pawl lever 1214 (pivoting about a transverse pivot pin 1214b), and a slidably disposed, nearly vertical defeat switch member 1216 in an upper region of the finger ring member 1204. A ratchet-toothed member 1218 is disposed in the thumb ring member 1202, proximally adjacent the pawl lever 1214. In the neutral/engaged position shown in FIG. 12A, a lower end 1214a of the pawl lever 1214 is engaged with the teeth of the ratchet-toothed member 1218. As depicted in FIG. 12B, in order to release the pawl lever 1214 from engagement with the ratchet-toothed member 1218, a user may depress the cam button 1212 in a proximal direction against the pawl lever 1214, which levers it (1214) away from the ratchet-toothed member 1218. FIG. 12C illustrates that the ratchet engagement may be defeated by depressing the cam button 1212 into the released state, and then sliding the defeat switch member 1216 up into engagement with a defeat-lock notch 1216a on the cam button 1212.

FIGS. 13A-13C illustrate a handle 1300 housing a ninth embodiment of a ratchet mechanism 1310, which is also a substantially internal mechanism. The handle 1300 includes a thumb ring member 1302 pivotably attached to a finger ring member 1304. The ratchet mechanism 1310 includes a slidably disposed cam button 1312, a pivotably disposed, nearly vertical pawl lever 1314 (pivoting about a transverse pivot pin 1314b), and a pivotably disposed defeat switch member 1316 in an upper region of the finger ring member 1304. A ratchet-toothed member 1318 is disposed in the thumb ring member 1302, proximally adjacent the pawl lever 1314. In the neutral/engaged position shown in FIG. 13A, a lower end 1314a of the pawl lever 1314 is engaged with the teeth of the ratchet-toothed member 1318. As depicted in FIG. 13B, in order to release the pawl lever 1314 from engagement with the ratchet-toothed member 1318, a user may depress the cam button 1312 in a proximal direction against the pawl lever 1314, which levers it (1314) about the transverse pivot pin 1314b such that the lower pawl lever $2^{nd}$ 1314a is disengaged from the ratchet-toothed member 1318. FIG. 13C illustrates that the ratchet engagement may be defeated by depressing the cam button 1312 into the released state, and then pivoting the defeat switch member 1316 such that its distal end 1316a engages with a defeat-lock notch 1312a on the cam button 1312.

Figure 14A:
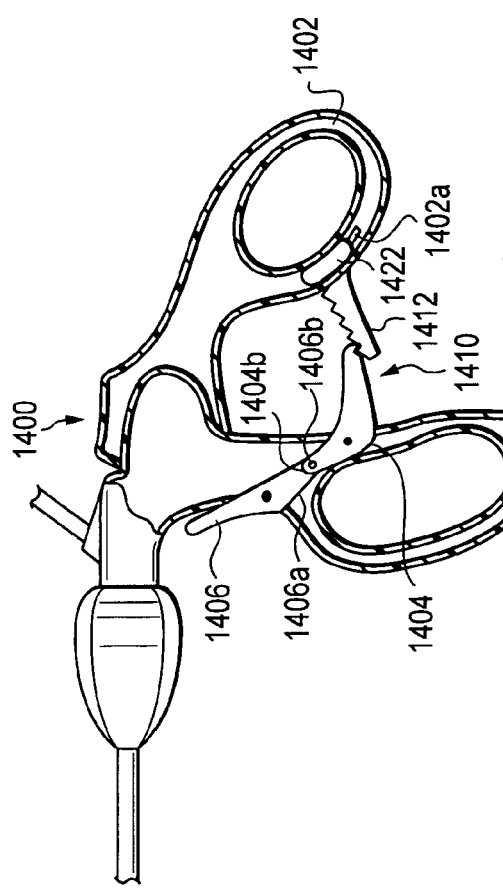
FIGS. 14A-14C show a handle housing a tenth ratchet mechanism embodiment.
Figure 14C:
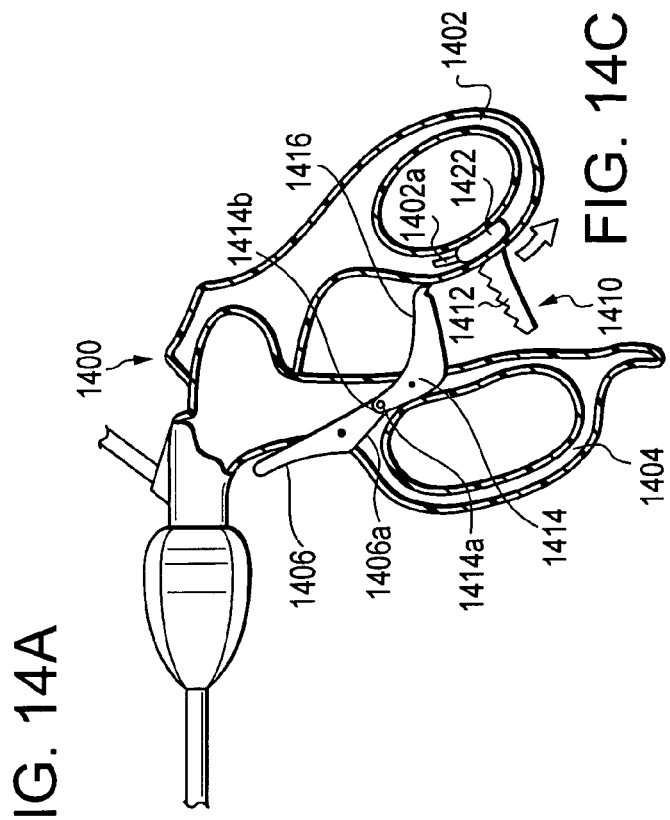
Figure 14B:
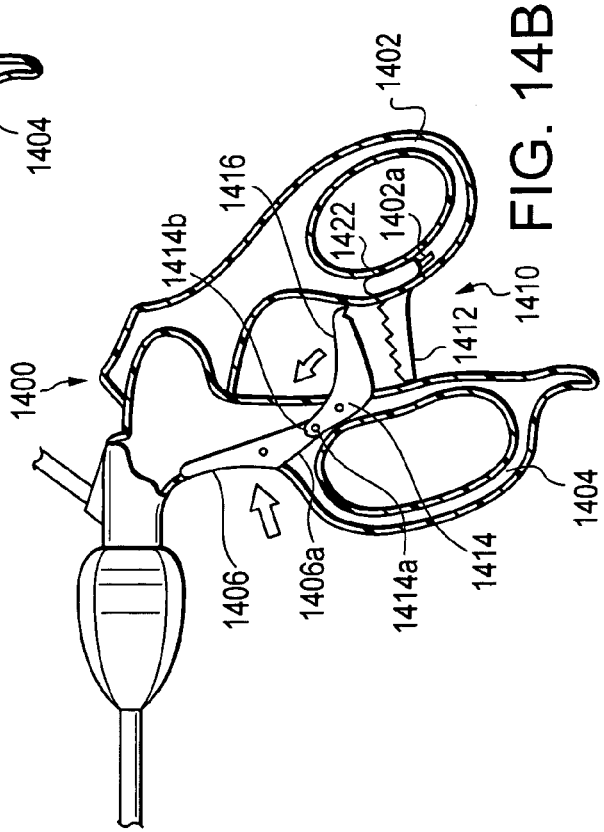

FIGS. 14A-14C illustrate a handle 1400 housing a tenth embodiment of a ratchet mechanism 1410. The handle includes a thumb ring member 1402 pivotably attached to a finger ring member 1404. The ratchet mechanism 1410 includes a curved ratchet-toothed arm 1412 projecting distally from the thumb ring member 1402 and slidably mounted therein. It (1410) also includes a release lever 1406 pivotably mounted to the finger ring member 1404 and a pawl member 1414 pivotably attached to the finger ring member 1404, the pawl member 1414 including a proximally projecting pawl arm 1416. The lower lever end 1406a of the release lever 1406 is engaged for slidable/pivotable operation with the upper end 1414a of the pawl member 1414 as a pin 1406b on the lower lever end 1406a engages a closed slot 1414b on the upper pawl member end 1414a. The thumb ring member 1402 includes a defeat slider button 1422 that is attached (through a groove 1402a) to the curved ratchet-toothed arm 1412, and which is configured to move the curved ratchet-toothed arm 1412 generally vertically relative to the thumb ring member 1402. In the neutral/engaged state illustrated in FIG. 14A, the pawl arm 1416 is biased into engagement (e.g., by a torsion spring) with the ratchet-toothed arm 1412, which is in an upper position within the groove 1402a. As illustrated in FIG. 14B the ratchet mechanism 1410 may be released by a user depressing the release lever 1406 such that its upper end 1414a moves generally proximally relative to the finger ring member 1404, which moves the lever pin 1406b in the pawl slot 1414b such that the pawl member 1414 pivots up and disengages the pawl arm 1416 from the ratchet-toothed arm 1412. In the ratchet-defeated state depicted in FIG. 14C, the defeat slider button 1422 is moved downward in the groove 1402a, defeating the engagement of the ratchet-toothed arm 1412 with the pawl arm 1416. As also shown in FIG. 14C, in this embodiment, it is not necessary to release the ratchet engagement (e.g., by depressing the release lever 1406) before defeating the ratchet mechanism 1410.

FIGS. 15A-15B illustrate a handle 1500 housing an eleventh embodiment of a ratchet mechanism 1510. The handle includes a thumb ring member 1502 pivotably attached to a finger ring member 1504. The ratchet mechanism 1510 includes a curved ratchet-toothed arm 1512 projecting distally from the thumb ring member 1502, a pawl arm 1514 pivotably attached to the finger ring member 1504, and a cam lever 1516 pivotably connected to the pawl arm 1514. A proximal end 1514a of the pawl arm 1514 preferably is biased into engagement with the ratchet-toothed arm 1512 (e.g., by a torsion or leaf spring, not shown). A distal end region of the pawl arm 1514 includes an elongate aperture 1514b that engages a transverse pin 1514c attached to the finger ring member 1504. In the neutral/engaged state illustrated in FIG. 15A, the proximal pawl arm end 1514a is engaged with the ratchet-toothed arm 1512, and the transverse pin 1514c is in the bottom end of the elongate aperture 1514b. To reach the ratchet-released state depicted in FIG. 15B, a user actuates the pawl arm 1514 proximally and slightly downward until the transverse pin 1514c is in the top end of the elongate aperture 1514b, which levers the proximal pawl arm end 1514 out of engagement from the ratchet-toothed arm 1512. To reach the ratchet-defeated state depicted in FIG. 15C, a user actuates the pawl arm 1514 into the released state, and then pivots the cam lever 1516 distally and downward. In the defeated state, it is preferable that the contact between the cam lever 1516, the pawl arm 1514, and the finger ring member 1504 be configured to form a frictional lock sufficient to resist the bias of the pawl arm 1514 toward engagement with the ratchet-toothed arm 1512.

Figure 16A:
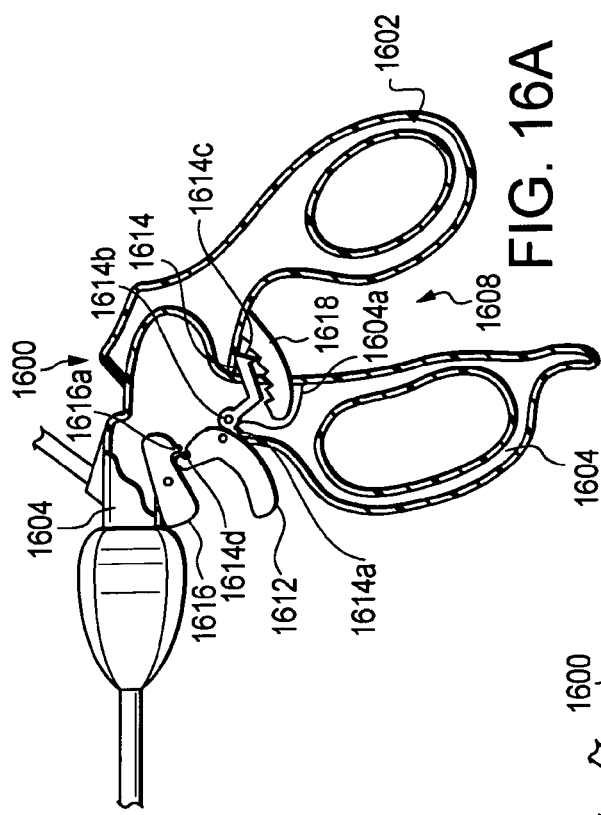
FIGS. 16A-16C show a handle housing a twelfth ratchet mechanism embodiment.
Figure 16C:
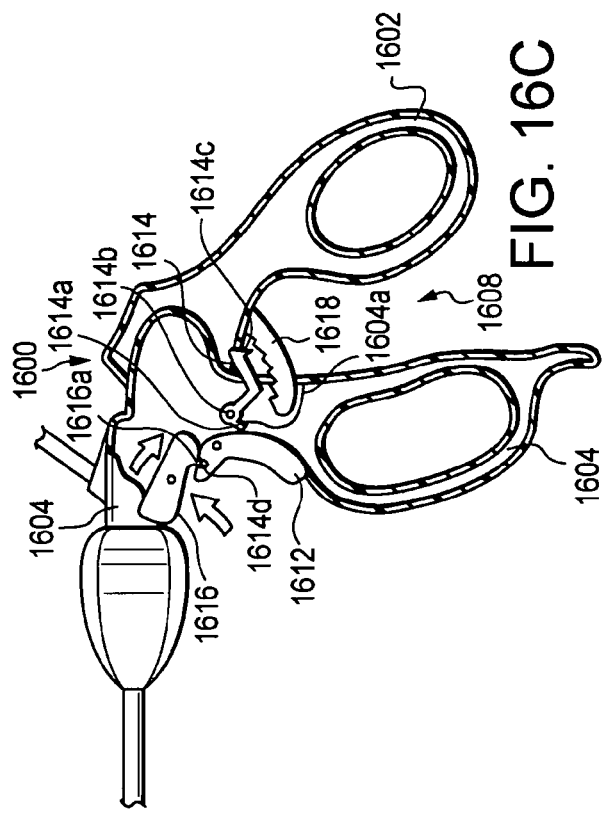
Figure 16B:
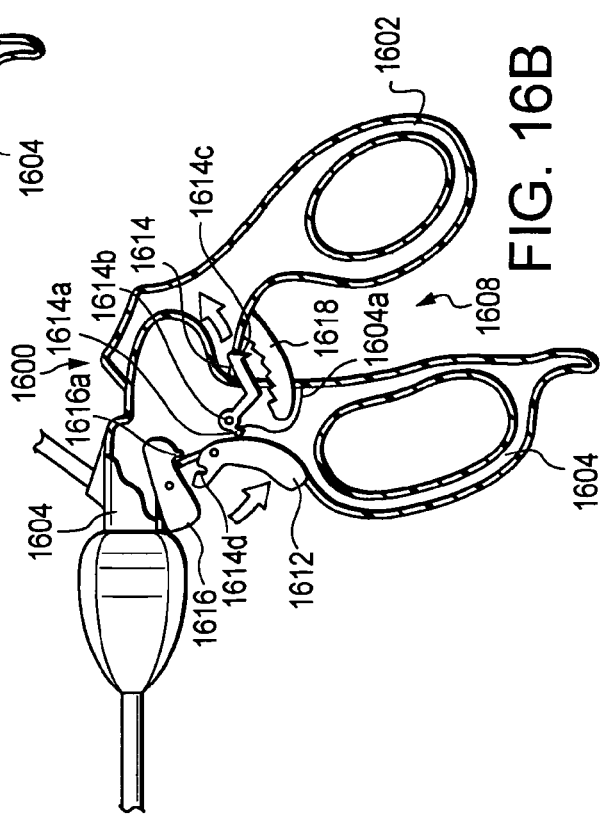

FIGS. 16A-16C illustrate a handle 1600 housing a twelfth embodiment of a ratchet mechanism 1608. The handle 1600 includes a thumb ring member 1602 pivotably attached to a finger ring member 1604. The ratchet mechanism 1608 includes a pivotably disposed cam trigger 1612, a pivotably disposed pawl member 1614 (pivoting about a transverse pivot pin 1614b), and a pivotably disposed defeat switch member 1616 in an upper, longitudinal region of the finger ring member 1604. A ratchet-toothed member 1618 is disposed in the thumb ring member 1602, proximally adjacent the pawl member 1614. The finger ring member 1604 includes a proximal cavity 1604a configured to receive a distal end portion of the ratchet-toothed member 1618 when the handle members 1602, 1604 are drawn together. The pawl member 1614 is generally L-shaped, with a small camming protrusion 1614a projecting distally from its upper end and is mounted on the pivot pin 1614b. In the neutral/engaged position shown in FIG. 16A, the pawl member 1614 preferably is biased (e.g., by a spring or other biasing means, not shown) such that a lower end 1614c is engaged with the teeth of the ratchet-toothed member 1618. As depicted in FIG. 16B, in order to release the pawl lever 1614 from engagement with the ratchet-toothed member 1618, a user may depress the cam trigger 1612 in a proximal direction against the camming protrusion 1614a of the pawl member 1614. The proximal surface of the cam trigger 1612 preferably is angled so that its contact with the camming protrusion 1614a levers the lower pawl member end 1614c away from the ratchet-toothed member 1618. FIG. 16C illustrates that the ratchet engagement may be defeated by depressing the cam trigger 1612 into the released state, and then pivoting the defeat switch member 1616 such that its proximal end 1616a engages with a defeat-lock notch 1614d on the cam trigger 1612.

FIGS. 17A-17C illustrate a handle 1700 housing a thirteenth embodiment of a ratchet mechanism 1708. The handle includes a thumb ring member 1702 pivotably attached to a finger ring member 1704. The ratchet mechanism 1708 includes a generally arcuate ratchet lever member 1710 that has a curved ratchet-toothed arm 1712 projecting generally proximally from the finger ring member 1704 and a trigger arm 1716 projecting generally distally from the finger ring member 1704. A defeat switch 1718 is disposed below and slightly distally from the trigger arm 1716. The ratchet lever member 1710 includes a pivoting connection 1710a to the finger ring member 1704, the connection 1710a being disposed near the longitudinal midpoint of both the ratchet lever member 1710 and the finger ring member 1704. The ratchet mechanism 1708 also includes a fixed pawl arm 1714 projecting generally distally from the thumb ring member 1702. The ratchet lever member 1710 preferably is biased (e.g., by a torsion or leaf spring, or other biasing means, not shown) such that the curved ratchet-toothed arm 1712 engages the pawl arm 1714 when the handle 1700 is in a neutral state as shown in FIG. 17A. In the ratchet-released state shown in FIG. 17B, a user depresses proximally the trigger arm 1716 of the ratchet lever member 1710, thereby levering the curved ratchet-toothed arm 1712 out of engagement with the pawl arm 1714. In the ratchet-defeated state depicted in FIG. 17C, the ratchet lever member 1710 is moved to the released state shown in FIG. 17B, then the user may pivot the defeat switch 1718 to contact the underside of the ratchet lever member 1710 to hold it (1710) in place. The defeat switch 1718 preferably includes a frictional or other locking means to maintain it in the released/defeated position (e.g., an internal locking spring, a pin-groove lock, or other locking means known to those of skill in the art).

Those of skill in the art will appreciate that there are known means for controlling the relative position/bias of the ratchet members disclosed above that are appropriate for use within the scope of the present invention, and that different materials may be useful in embodiments of the present invention. Those of skill in the art will also appreciate that, for handle embodiments of the present invention, the thumb ring member and/or the finger ring member may not actually require a closed ring structure, but may include an open ring or other-shaped support structure for a user's thumb and fingers, respectively. It is intended that the foregoing detailed description be regarded as illustrative rather than limiting. It should be understood that the following claims, including all equivalents, are intended to define the spirit and scope of this invention.

We claim:

1. A surgical instrument having a handle operatively connected to an elongate shaft, the handle comprising:
   a thumb ring member pivotably connected to a finger ring member;
   a first engagement member fixed in and projecting generally distally from the thumb ring member;
   a second engagement member pivotably mounted to and projecting generally proximally from the finger ring member, a first end portion of the second engagement member being biased into engagement with the first engagement member and defining an engaged state; and
   an elongate cam member pivotably connected to the finger ring member and comprising an operative contact with a second end portion of the second engagement member;
   wherein, the elongate cam member is at a first angle relative to the second engagement member, the operative contact is sufficient to pivot the second engagement member so as to overcome the biased engagement of the second engagement member with the first engagement member defining a released state;
   wherein, when the elongate cam member is at a second angle relative to the second engagement member, the operative contact is sufficient to pivot the second engagement member so as to overcome the biased engagement of the second engagement member with the first engagement member and is sufficient to bias the second engagement member out of engagement with the first engagement member defining a defeated state; and wherein the elongate cam member, first engagement member, and second engagement member are configured such that, when the handle occupies the engaged state, the elongate cam member is disposed intermediate the first angle and the second angle.

2. The surgical instrument of claim 1, wherein the operative contact of the handle to the elongate shaft comprises:

an externally indexed rotation knob attached to an exterior surface of the elongate shaft, the knob configured to rotate the elongate shaft around its longitudinal axis; and a rotation-permitting retaining connection of the second handle member to the elongate shaft.

3. The surgical instrument of claim 2, further comprising:

an indexed detent connection of the second handle member to the elongate shaft, the indexed detent connection comprising:

a ball detent disposed in a cavity adjacent a distal end of the second handle member;

a longitudinally grooved exterior surface portion near the proximal end of the elongate shaft; and an o-ring, said o-ring retaining the ball detent in the cavity and biasing the ball detent into indexing contact with the longitudinally grooved exterior surface portion of the elongate shaft.

4. The surgical instrument of claim 1, wherein the elongate shaft comprises an actuation rod extending longitudinally therethrough and the actuation rod includes a proximal-end rod-retention structure that is of greater diameter than a majority length of the actuation rod; and the thumb ring member comprising an actuation rod retainer, the actuation rod retainer including a distal keyhole groove configured to retain the proximal-end retention structure.

5. The surgical instrument of claim 4, further comprising a generally tubular bearing member disposed at least partially around a proximal portion of the actuation rod.

6. The surgical instrument of claim 5, wherein the generally tubular bearing member provides electrical insulation around at least a proximal portion of the actuation rod.

7. The surgical instrument of claim 5, wherein the generally tubular bearing member comprises a connector for retaining the actuation rod.

8. The surgical instrument of claim 4, further comprising an electrode in conductive contact with the actuation rod.

9. The surgical instrument of claim 4, wherein the proximal-end rod-retention structure is generally spherical.

10. The surgical instrument of claim 4, wherein a metal insert is disposed in the distal keyhole groove.

11. The surgical instrument of claim 1, wherein the elongate shaft comprises an actuation rod extending longitudinally therethrough and a longitudinally grooved exterior surface portion near the proximal end of the elongate shaft.

12. The surgical instrument of claim 11, wherein the finger ring member comprises a generally cylindrical bearing component disposed in an upper region thereof, the bearing component comprising:

a central longitudinal lumen through which a proximal portion of the actuation rod fully extends, a distal portion of said lumen disposed around a longitudinally grooved exterior proximal portion of the elongate shaft;

a ball detent disposed in a cavity in the distal portion of the bearing; and a groove immediately adjacent the cavity, said groove seating an o-ring, and said o-ring being configured to retain the ball detent in the cavity and to bias the ball detent into indexing contact with the longitudinally grooved exterior proximal portion of the elongate shaft.

13. The surgical instrument of claim 12, wherein the elongate shaft is retained in the distal portion of said lumen by a threaded connector.

14. The surgical instrument of claim 1, further comprising a cushioning insert disposed on a region selected from the finger ring member, the thumb ring member, or both.

15. The surgical instrument of claim 1, further comprising a finger rest projecting generally downward from the finger ring member.

16. The surgical instrument of claim 1, further comprising a textured surface on an upper proximal surface of the thumb ring member.

17. The surgical instrument of claim 1, further comprising a textured surface on an intermediate side surface of the thumb ring member.

18. The surgical instrument of claim 1, wherein an upper portion of the thumb ring member and an upper portion of the finger ring member are configured and coupled such that an actuation rod disposed slidingly through the finger ring member and connected to the thumb ring portion is shielded from contact by a hand of a user.

19. A surgical instrument having a handle operatively connected to an elongate shaft according to claim 1, wherein:

the thumb ring member comprising a plurality of raised thumb-grip ridges disposed on an upper proximal surface of the thumb ring member, said ridges configured to provide a frictional gripping surface.

20. A surgical instrument having a handle operatively connected to an elongate shaft according to claim 1, wherein:

the thumb ring member comprising a plurality of raised thumb-grip ridges disposed on an intermediate side surface of the thumb ring member, said ridges configured to provide a frictional gripping surface.

21. A surgical instrument having a handle operatively connected to an elongate shaft, the handle comprising:

a first handle member pivotably connected to a second handle member; and a ratchet mechanism removably engaging the first and second handle members, the ratchet mechanism comprising:

a ratchet-toothed engagement member fixed to and projecting generally distally from the first handle member;

an L-shaped pawl member having a camming leg portion and a pawl leg portion generally perpendicular to the camming leg portion, the L-shaped pawl member pivotably mounted in the second handle member such that the pawl leg portion projects generally proximally from the second handle member, an upper region of the camming leg portion comprising a generally vertical camming surface and a distally projecting camming surface;

a cam lever;

a biasing spring mounted in the second handle member and operatively contacting the L-shaped pawl member such that a proximal end region of the pawl leg portion is biased into engagement with the ratchet-toothed engagement member when the cam lever is disposed at a neutral angle; and the cam lever pivotably connected to the second handle member, the cam lever comprising a first operative contact with the L-shaped pawl member such that when the cam member is disposed at a first angle relative to the L-shaped pawl member, the first operative contact is between the cam lever and the distally projecting camming surface, said first operative contact being sufficient to pivot the L-shaped pawl member so as to overcome and release the biased engagement of the pawl leg portion with the ratchet-toothed engagement member; and wherein, when the cam lever is disposed at a second angle relative to the L-shaped pawl member, a second operative contact between the cam lever and the generally vertical camming surface is sufficient to pivot the L-shaped pawl member so as to overcome and defeat the biased engagement of the pawl leg portion with the ratchet-toothed engagement member and is also sufficient to bias the L-shaped pawl member at an angle wherein the pawl leg portion is not engaged with the ratchet-toothed engagement member; and wherein the neutral angle of the cam lever is between the first angle and the second angle relative to the L-shaped pawl member.

22. A method of use of a surgical instrument, the method comprising the steps of:

providing a surgical instrument having a handle, the surgical instrument handle comprising a thumb ring member pivotably connected to a finger ring member;

a ratchet-toothed arm fixed in and projecting generally distally from the thumb ring member;

an L-shaped pawl member pivotably mounted to and comprising a first end portion projecting generally proximally from the finger ring member; and a cam lever pivotably connected to the finger ring member and comprising an operative contact with a second end portion of the pawl member, the first end portion of the pawl member being spring-biased by a spring into engagement with the ratchet-toothed arm when the cam lever is at a default first angle relative to the finger ring member;

pivoting the cam lever to a second angle relative to the finger ring member, wherein the operative contact is sufficient to pivot the pawl member so as to overcome the spring bias and release the engagement of the first end portion of the pawl member with the ratchet-toothed arm; and pivoting the cam lever to a third angle relative to the finger ring member so that the spring biases the second end portion of the pawl member against the cam lever such that the engagement of the first end portion of the pawl member with the ratchet-toothed arm is defeated, wherein the position of the cam lever at the default first angle is between position of the cam lever at the second angle and at the third angle.

23. A surgical instrument having a handle ratchet mechanism with a single-button release/defeat feature, the handle ratchet mechanism comprising:

a first engagement member;

a second engagement member pivotably mounted to a handle portion and projecting toward the first engagement member;

a spring member biasing a first end portion of the second engagement member into engagement with the first engagement member; and a cam button pivotably connected to the handle portion and comprising an operative contact with a second end portion of the second engagement member;

wherein, when the cam button is at a first angle relative to the second engagement member, the operative contact is sufficient to pivot the second engagement member so as to overcome the biased engagement of the second engagement member with the first engagement member;

wherein, when the cam button is at a second angle relative to the second engagement member, the operative contact is sufficient to pivot the second engagement member so as to overcome the biased engagement of the second engagement member with the first engagement member and is sufficient to bias the second engagement member out of engagement with the first engagement member; and wherein when the cam button is at a third angle, between the first and second angles, the operative contact permits the biased engagement of the second engagement member with the first engagement member.

24. A surgical instrument having a handle operatively connected to an elongate shaft, the handle comprising:

a thumb ring member pivotably connected to a finger ring member;

a toothed first engagement member comprised by the thumb ring member;

a second engagement member pivotably mounted in the finger ring member; and an elongate cam member movably connected to the finger ring member and comprising an operative contact with a second end portion of the second engagement member;

wherein a first end portion of the second engagement member is biased into engagement with the toothed first engagement member by a spring member when the elongate cam member is disposed in a neutral position;

wherein, when the elongate cam member is in a first position relative to the second engagement member, the operative contact is sufficient to move the second engagement member such that the operative contact provides a force sufficient to overcome the biased engagement of the second engagement member with the toothed first engagement member;

wherein, when the elongate cam member is in a second position relative to the second engagement member, the operative contact is sufficient to move the second engagement member so as to overcome the biased engagement of the second engagement member with the first engagement member and is sufficient to bias the second engagement member out of engagement with the first engagement member; and wherein the neutral position of the elongate cam member is between the first position and the second position.

* * * * *